United States Patent
Kawabe et al.

(10) Patent No.: US 10,765,377 B2
(45) Date of Patent: Sep. 8, 2020

(54) HEARTBEAT-SIGNAL DETECTING DEVICE

(71) Applicant: NATIONAL UNIVERSITY CORPORATION TOKAI NATIONAL HIGHER EDUCATION, Nagoya-shi, Aichi (JP)

(72) Inventors: Tsutomu Kawabe, Nagoya (JP); Mitsuhiro Shikida, Nagoya (JP); Miyoko Matsushima, Nagoya (JP)

(73) Assignee: NATIONAL UNIVERSITY CORPORATION TOKAI NATIONAL HIGHER EDUCATION AND RESEARCH SYSTEM, Nagoya-shi (JP)

( * ) Notice: Subject to any disclaimer, the term of this patent is extended or adjusted under 35 U.S.C. 154(b) by 413 days.

(21) Appl. No.: 15/548,286

(22) PCT Filed: Feb. 3, 2016

(86) PCT No.: PCT/JP2016/053293
§ 371 (c)(1),
(2) Date: Aug. 2, 2017

(87) PCT Pub. No.: WO2016/125842
PCT Pub. Date: Aug. 11, 2016

(65) Prior Publication Data
US 2018/0014792 A1  Jan. 18, 2018

(30) Foreign Application Priority Data

Feb. 3, 2015  (JP) .................................. 2015-019747
Feb. 3, 2015  (JP) .................................. 2015-019748

(51) Int. Cl.
*A61B 5/00* (2006.01)
*A61B 1/273* (2006.01)
(Continued)

(52) U.S. Cl.
CPC .......... *A61B 5/7278* (2013.01); *A61B 1/2676* (2013.01); *A61B 1/273* (2013.01);
(Continued)

(58) Field of Classification Search
CPC ..... A61B 1/2676; A61B 1/273; A61B 5/0245; A61B 5/7257; A61B 5/6852;
(Continued)

(56) References Cited

U.S. PATENT DOCUMENTS

2002/0045837 A1    4/2002  Wei et al.
2007/0017285 A1*   1/2007  Wang ................... G01F 1/6845
                                                         73/204.26
(Continued)

FOREIGN PATENT DOCUMENTS

EP    0 651 971 A1    5/1995
GB    2462304 A       2/2010
(Continued)

OTHER PUBLICATIONS

May 10, 2016 Search Report issued in International Patent Application No. PCT/JP2016/053293.
(Continued)

*Primary Examiner* — Catherine M Voorhees
*Assistant Examiner* — Roland Dinga
(74) *Attorney, Agent, or Firm* — Oliff PLC

(57) ABSTRACT

A heartbeat-signal detecting device, which is for detecting a heartbeat signal of a living body, includes: (a) a gas-flow sensor configured to detect a flow rate of exhalation and inhalation passing through a trachea of the living body; (b) a gas-flow calculation controlling portion configured to output a respiration signal that reflects a respiratory motion of the living body, based on a signal outputted from the gas-flow sensor; (c) a waveform analysis controlling portion configured to extract, from the respiration signal, frequency
(Continued)

components which are in synchronization with a pulse of a heart of the living body superimposed on the respiration signal, and to output a heartbeat signal representing a heartbeat waveform of the living body; and (d) a heartbeat-signal evaluation controlling portion is configured to evaluate a functional abnormality or an anatomic abnormality of the heart, based on the heartbeat signal analyzed by the waveform analysis controlling portion.

7 Claims, 23 Drawing Sheets

(51) Int. Cl.
| | | |
|---|---|---|
| *A61B 5/0245* | (2006.01) | |
| *G01F 1/68* | (2006.01) | |
| *A61B 1/267* | (2006.01) | |
| *A61B 5/024* | (2006.01) | |
| *A61B 5/087* | (2006.01) | |
| *G01F 1/69* | (2006.01) | |

(52) U.S. Cl.
CPC ............ *A61B 5/024* (2013.01); *A61B 5/0245* (2013.01); *A61B 5/087* (2013.01); *A61B 5/6803* (2013.01); *A61B 5/6852* (2013.01); *A61B 5/7257* (2013.01); *G01F 1/68* (2013.01); *G01F 1/69* (2013.01)

(58) Field of Classification Search
CPC ....... A61B 5/6803; A61B 5/087; A61B 5/024; G01F 1/68; G01F 1/69
See application file for complete search history.

(56) References Cited

U.S. PATENT DOCUMENTS

| | | | | |
|---|---|---|---|---|
| 2008/0045813 | A1* | 2/2008 | Phuah | ................ A61B 5/0205 600/301 |
| 2015/0182713 | A1 | 7/2015 | Phuah et al. | |

FOREIGN PATENT DOCUMENTS

| | | | |
|---|---|---|---|
| JP | 2001-198097 | A | 7/2001 |
| JP | 2002-034943 | A | 2/2002 |
| JP | 2007-525267 | A | 9/2007 |
| JP | 2009-168480 | A | 7/2009 |
| WO | 95/10980 | A1 | 4/1995 |

OTHER PUBLICATIONS

Aug. 10, 2018 Extended Search Report issued in European Patent Application No. 16746673.9.

Jun. 26, 2019 Office Action issued in European Patent Application No. 16746673.9.

* cited by examiner

HEARTBEAT-SIGNAL DETECTING DEVICE

TECHNICAL FIELD

The present invention relates to a heartbeat-signal detecting device which is capable of easily detecting a heartbeat signal reflecting an ejection action of a heart of a living body, more preferably, and which is capable of also evaluating a physiological function of the heart, without using electrodes attached to the living body.

BACKGROUND ART

The heartbeat signal of the living body is important information of the living body. Conventionally, there has been used an electrocardiographic induction device that detects, as the heartbeat signal, an electrocardiogram obtained through a plurality of ECG electrodes attached to the living body. For example, devices disclosed in Patent Documents 1 and 2 are examples of such a device. The electrocardiogram is called as electrocardiographic induction waveform or ECG waveform, and R wave contained in the electrocardiogram is characterized to have a considerably clear pulse shape, so as to be easily detectable. Thus, the electrocardiogram obtains reliability as a substitution as the heartbeat signal in general monitoring of a patient at a medical site.

PRIOR ART DOCUMENT

Patent Document

[Patent Document 1] JP 2001-198097 A
[Patent Document 2] JP 2002-034943 A

DISCLOSURE OF THE INVENTION

Object to be Achieved by the Invention

However, in a case where the patient is an infant, there is a problem that it is difficult to keep the ECG electrodes attached to his or her skin for a long time for the purpose of electrocardiograph measurement because the skin of an infant is delicate. Further, there is another problem that the electrocardiographic induction waveform does not reflect a cardiac output, i.e., an actual volumetric change of a heart, and the generation of the electrocardiographic induction waveform does not necessarily indicate an ejection action of the heart, for example, in case of pulseless electrical activity, so that it cannot be always considered reliable as the heartbeat signal on an emergency lifesaving site. Moreover, there is still another problem that it is difficult to make a clinical evaluation of a circulatory system drug that changes not only a heart rate but also a cardiac output, by only using the electrocardiographic induction waveform.

The present invention was made in view of the background discussed above. It is therefore an object of the present invention to provide a heartbeat-signal detecting device which is capable of easily detecting a heartbeat signal reflecting an ejection action of a heart of a living body, more preferably, also a cardiac output, without using electrodes attached to the living body.

After having made various studies under the above-described background, the present inventor, etc. studied, in detail, about a respiratory waveform or ventilatory waveform of lungs of a living body which indicates a time-dependent change of a rate of air inspired into the lungs and a rate of air expired from the lungs, and found out that a pulsating component pulsating in synchronization with a heartbeat is superimposed on the ventilatory waveform of the lungs, and that the pulsating component of the lungs corresponds to a volumetric change of the heart. The lungs and the heart are accommodated within a thoracic cavity that is isolated by a thorax having a relatively high rigidity and a thoracic diaphragm closing a lower opening of the thorax, wherein the thorax is surrounded by ribs, a sternum and thoracic vertebrae. Although the volumetric change of the heart, which is caused by a pulse, is smaller than a volumetric change of the lungs, which is caused by a respiratory motion, the cycle of the volumetric change of the heart is short so that the volumetric change of the heart is clearly superimposed on the ventilatory waveform of the lungs. Thus, the present inventor, etc. found out that, if the ventilatory waveform that is a flow rate of the gas passing through an airway including a mouth and a nasal cavity of a living body is detected, the heartbeat signal can be extracted from the detected ventilatory waveform. The present invention was made based on such a finding.

Measures for Achieving the Object and Effect

That is, the essence of the invention is, in (a) a heartbeat-signal detecting device for detecting a heartbeat signal of a living body, characterized by comprising: (b) a gas-flow sensor configured to detect flows of exhalation and inhalation of the living body; (c) a gas-flow calculation controlling portion configured to output a respiration signal that reflects a respiratory motion of the living body, based on a signal outputted from the gas-flow sensor; and (d) a waveform analysis controlling portion configured to extract, from the respiration signal outputted from the gas-flow calculation controlling portion, frequency components which are in synchronization with a pulse of a heart of the living body superimposed on the respiration signal, and to output a heartbeat signal representing the pulse.

Effects of the Invention

In this arrangement, the frequency components, which are in synchronization with the pulse of the heart of the living body superimposed on the respiration signal, are extracted from the respiration signal outputted from the gas-flow calculation controlling portion, by the waveform analysis controlling portion, and the heartbeat signal representing the pulse is outputted. Thus, the heartbeat signal reflecting the ejection action of the heart of the living body can be easily detected by using the heartbeat signal, without using ECG electrodes attached to the living body. That is, the heartbeat signal can be easily obtained even in a case of an infant where it is difficult to keep the ECG electrodes attached to his or her skin for a long time for the purpose of electrocardiograph measurement because the skin is delicate. Further, the heartbeat signal reflecting a cardiac output, i.e., an actual volumetric change of the heart can be obtained, and therefore, as compared with a conventional device using an electrocardiographic induction waveform, it is advantageously possible to confirm the presence or absence of a pulse of the heart with higher reliability, perform quickly a medical treatment at an emergency lifesaving site, and evaluate clinically a circulatory system drug that changes not only a heart rate but also a cardiac output.

Preferably, the gas-flow sensor may be provided in a trachea, a nasal cavity, outside of the living body or any other position that makes it possible to detect a gas flow of the living body such as exhalation and inhalation. For example, in case of use of an endotracheal intubation tube inserted into the trachea of the living body, the gas-flow sensor is provided in the endotracheal intubation tube or in outside of the living body such as a connection tube interconnecting between the endotracheal intubation tube and an artificial respirator. In case of use of a nasal cannula or a mask disposed to cover a nose and a mouth of the living body, the gas-flow sensor is provided in the nasal cannula, the mask or a connection tube interconnecting between the nasal cannula or mask and an artificial respirator.

Preferably, the gas-flow sensor is configured to detect a flow speed of the gas passing through a tube, based on a change of an electric resistance of a heater element that is heated by electricity supplied thereto, wherein the electric resistance is changed depending on the flow speed. The heater element is constituted by an electric resistance element whose electric resistance is changed depending on a temperature, wherein the electric resistance is constituted by, for example, a platinum resistance element or a gold resistance element. The heater element is provided on an inner surface of a circuit substrate film which is disposed along an inner wall surface of the tube and which is spaced apart from the inner wall surface by a predetermined space. Further, preferably, a space is provided between the heater and the tube, to insulate heat transmission from the heater to the tube. Owing to this construction, even where the tube is made of a flexible material, since the heater is provided on the inner wall surface of the tube so as to extend along a shape of the inner wall surface and to be spaced apart from the inner wall surface by the predetermined space, the gas flow speed can be detected in an area having a certain distance, rather than being detected at a point, so that the flow rate can be measured even if the tube is curvy. Further, owing to the provision of the space for insulating the heat transmission between the heater and the tube, the responsiveness with respect to the heat is dependent on a heat capacity of the heater itself, thereby consequently making it possible to realize a high-speed response of 100 milliseconds or less.

Preferably, the heartbeat-signal detecting device comprises: a gas-flow-speed measuring circuit including a bridge circuit (electric bridge) that includes four resistance elements, each of one or two of the four resistance elements being constituted by the heater element; and a gas-flow calculation controlling portion configured to calculate the flow rate or the flow speed in accordance with a pre-stored relationship between the flow rate or the flow speed and an output signal of the gas-flow-speed measuring circuit that reflects a resistance value of the heater element, and based on the output signal of the gas-flow-speed measuring circuit.

Preferably, the waveform analysis controlling portion is configured to remove, from the respiration signal outputted from the gas-flow calculation controlling portion, the frequency components which are in synchronization with the pulse of the heart of the living body superimposed on the respiration signal, and output a ventilation component signal representing a lung capacity component originating from a thorax and a thoracic diaphragm of the living body. This arrangement enables the respiration signal and the heartbeat signal to be simultaneously obtained, whereby respiration and heart beat reflecting heart functions can be monitored by a single device. Thus, medical services can be performed in a short time at an emergency medical site with limitations in time, place and personnel.

Preferably, the heartbeat-signal detecting device comprises a heartbeat-signal evaluation controlling portion is configured to evaluate a functional abnormality or an anatomic abnormality of two atria and two ventricles constituting the heart, based on the heartbeat signal analyzed by the waveform analysis controlling portion. This heartbeat-signal evaluation controlling portion calculates a correlation coefficient between the heartbeat signal analyzed by the waveform analysis controlling portion and a pre-stored abnormality evaluation pattern, and evaluates the functional abnormality or anatomic abnormality of the two atria and two ventricles constituting the heart, based on an excess of the correlation coefficient over a preset determination value. Owing to this arrangement, not only the heartbeat signal can be obtained but also the functional abnormality or anatomic abnormality of the two atria and two ventricles constituting the heart can be known based on the heartbeat signal.

Preferably, in (a) an airway gas-flow rate measuring device for measuring a flow rate of a gas passing through an airway in a distal end portion of a flexible sheath, the airway gas-flow rate measuring device comprises: the above-described gas-flow sensor; (b) a first sensor substrate provided integrally or independently in a distal end portion of a gas-flow measuring catheter that passes through the flexible sheath; (c) a flexible first circuit substrate film wound on an outer circumferential surface of the first sensor substrate such that the first circuit substrate film has a cylindrical shape and is fixed to the outer circumferential surface of the first sensor substrate; (d) a gas-flow sensor including one first heater element that is provided on an outer circumferential surface of the first circuit substrate film or two first heater elements that are provided on the outer circumferential surface of the first circuit substrate film; (e) an operating wire provided to pass through the gas-flow measuring catheter; and (f) a diameter expansion basket constituted by a plurality of elastic wires bundled at distal and rear end portions thereof to each other, and provided in a distal end portion of the operating wire, the diameter expansion basket having a diameter that is increased when the diameter expansion basket is caused to protrude from a distal end of the gas-flow measuring catheter. In the thus constructed airway gas-flow rate measuring device, the first heater element or elements are provided on the outer circumferential surface of the flexible first circuit substrate film, which is wound on the outer circumferential surface of the first sensor substrate such that the first circuit substrate film has the cylindrical shape and is fixed to the outer circumferential surface of the first sensor substrate, and the diameter expansion basket, whose diameter is increased with the operating wire passing through the fluid measuring catheter being operatively caused to protrude, causes the first gas-flow sensor to be positioned in a center of the airway. Thus, as compared with a conventional type in which the measured gas is caused to pass between a vent hole, which is formed in a side face of a cylindrical sensor substrate that is fixed at one of its opposite ends to a catheter, and an opening of the other of the opposite ends of the cylindrical sensor substrate, it is possible to establish a construction which reduces a flow resistance in the airway and which hardly causes retention of a viscous liquid in the airway and clogging of the airway, whereby the measurement of the gas-flow rate can be made accurately and easily.

Preferably, in (a) an airway gas-flow rate measuring device for measuring a flow rate of a gas passing through an airway in a distal end portion of a flexible sheath, the airway gas-flow rate measuring device comprises: the above-described gas-flow sensor; (b) an operating wire provided to pass through the gas-flow measuring catheter; (c) a diameter expansion basket constituted by a plurality of elastic wires bundled at distal and rear end portions thereof to each other, and provided in a distal end portion of the operating wire, the diameter expansion basket having a diameter that is increased when the diameter expansion basket is caused to protrude from a distal end of the gas-flow measuring catheter, (d) a second sensor substrate having a columnar shape or a cylindrical shape and provided in a distal end portion of the diameter expansion basket; (e) a flexible second circuit substrate film wound on an outer circumferential surface of the second sensor substrate such that the second circuit substrate film has a cylindrical shape and is fixed to the outer circumferential surface of the second sensor substrate; and (f) a gas-flow sensor including one second heater element that is provided on an outer circumferential surface of the second circuit substrate film or two second heater elements that are provided on the outer circumferential surface of the second circuit substrate film. In the thus constructed airway gas-flow rate measuring device, the second heater element or elements are provided on the outer circumferential surface of the flexible second circuit substrate film, which is wound on the outer circumferential surface of the second sensor substrate such that the second circuit substrate film has the cylindrical shape and is fixed to the outer circumferential surface of the second sensor substrate, and the diameter expansion basket, whose diameter is increased with the operating wire passing through the fluid measuring catheter being operatively caused to protrude, causes the second gas-flow sensor to be positioned in a center of the airway. Thus, as compared with a conventional type in which the measured gas is caused to pass between a vent hole, which is formed in a side face of a cylindrical sensor substrate that is fixed at one of its opposite ends to a catheter, and an opening of the other of the opposite ends of the cylindrical sensor substrate, it is possible to establish a construction which reduces a flow resistance in the airway and which hardly causes retention of a viscous liquid in the airway and clogging of the airway, whereby the measurement of the gas-flow rate can be made accurately and easily.

Preferably, in (a) an airway gas-flow rate measuring device for measuring a flow rate of a gas passing through an airway in a distal end portion of a flexible sheath, the airway gas-flow rate measuring device comprises: the above-described gas-flow sensor, (b) a first sensor substrate provided integrally or independently in a distal end portion of the gas-flow measuring catheter; (c) a flexible first circuit substrate film wound on an outer circumferential surface of the first sensor substrate such that the first circuit substrate film has a cylindrical shape and is fixed to the outer circumferential surface of the first sensor substrate; (d) a first gas-flow sensor including one first heater element that is provided on an outer circumferential surface of the first circuit substrate film or two first heater elements that are provided on the outer circumferential surface of the first circuit substrate film; an operating wire provided to pass through the gas-flow measuring catheter; (e) a diameter expansion basket constituted by a plurality of elastic wires bundled at distal and rear end portions thereof to each other, and provided in a distal end portion of the operating wire, the diameter expansion basket having a diameter that is increased when the diameter expansion basket is caused to protrude from a distal end of the gas-flow measuring catheter; (f) a second sensor substrate having a columnar shape or a cylindrical shape and provided in a distal end portion of the diameter expansion basket; (g) a flexible second circuit substrate film wound on an outer circumferential surface of the second sensor substrate such that the second circuit substrate film has a cylindrical shape and is fixed to the outer circumferential surface of the second sensor substrate; and (h) a second gas-flow sensor including one second heater element that is provided on an outer circumferential surface of the second circuit substrate film or two second heater elements that are provided on the outer circumferential surface of the second circuit substrate film. In the thus constructed airway gas-flow rate measuring device, the first heater element or elements are provided on the outer circumferential surface of the flexible first circuit substrate film, which is wound on the outer circumferential surface of the first sensor substrate such that the first circuit substrate film has the cylindrical shape and is fixed to the outer circumferential surface of the first sensor substrate, while the second heater element or elements are provided on the outer circumferential surface of the flexible second circuit substrate film, which is wound on the outer circumferential surface of the second sensor substrate such that the second circuit substrate film has the cylindrical shape and is fixed to the outer circumferential surface of the second sensor substrate. Further, the diameter expansion basket, whose diameter is increased with the operating wire passing through the fluid measuring catheter being operatively caused to protrude, causes the first and second gas-flow sensors to be positioned in a center of the airway. Thus, as compared with a conventional type in which the measured gas is caused to pass between a vent hole, which is formed in a side face of a cylindrical sensor substrate that is fixed at one of its opposite ends to a catheter, and an opening of the other of the opposite ends of the cylindrical sensor substrate, it is possible to establish a construction which reduces a flow resistance in the airway and which hardly causes retention of a viscous liquid in the airway and clogging of the airway, whereby the measurement of the gas-flow rate can be made accurately and easily. Further, since the first and second gas-flow sensors are provided on respective opposite sides of the diameter expansion basket in the airway, it is possible to measure the flow rate by using one of the first and second heater elements which is located on an upstream side, as viewed in a direction of the gas flow, of the other in the airway, thereby enabling the flow rate to be more accurately measured by using a gas flow which is not disturbed by the diameter expansion basket and which does not contain temperature noise caused by the upstream-side heater element.

Preferably, the flexible first circuit substrate film is fixedly wound on the outer circumferential surface of the first sensor substrate via a spacer, such that a space is defined between an outer circumferential surface of the first sensor substrate and at least a portion or portions of the first circuit substrate film in which the one or two first heater elements are provided. Owing to this arrangement, the first sensor substrate is thermally insulated from the first heater element or elements provided on the first circuit substrate film by an increased degree, whereby the gas-flow rate can be more accurately measured. Further, the responsiveness with respect to the heat is dependent on a heat capacity of the first heater element or elements themselves, thereby making it possible to obtain a high-speed response.

Preferably, the flexible second circuit substrate film is fixedly wound on the outer circumferential surface of the second sensor substrate via a spacer, such that a space is defined between an outer circumferential surface of the second sensor substrate and at least a portion or portions of the second circuit substrate film in which the one or two heater elements are provided. Owing to this arrangement, the second sensor substrate is thermally insulated from the second heater element or elements provided on the second circuit substrate film by an increased degree, whereby the gas-flow rate can be more accurately measured. Further, the responsiveness with respect to the heat is dependent on a heat capacity of the second heater element or elements themselves, thereby making it possible to obtain a high-speed response.

Preferably, the first circuit substrate film is provided with the two first heater elements as a pair of first heater elements formed thereon. Further, the airway gas-flow rate measuring device comprises: a first gas-flow-speed measuring circuit including a pair of bridge circuits and a differential amplifier, each of the bridge circuits consisting of four resistance elements that include a corresponding one of the two first heater elements, the differential amplifier being configured to output an output signal corresponding to a difference between output signals of the bridge circuits; and a first gas-flow-rate calculation controlling portion configured to calculate a first gas-flow-rate signal representing a flow rate of the gas passing through the airway, in accordance with a pre-stored relationship and based on the output signal outputted by the first gas-flow-speed measuring circuit. The first gas-flow rate signal represents the direction of the gas flow through the airway in one respiratory cycle, by one peak and one trough. Thus, irrespective of the direction of the gas flow through the airway, it is possible to obtain easily understandable information indicative of the direction of the gas flow through the airway. Further, the gas-flow rate can be calculated from the output of one of the bridge circuits having the heater element located on the upstream side as viewed in the direction of the gas flow.

Preferably, the second circuit substrate film is provided with the two second heater elements as a pair of second heater elements formed thereon. Further, the airway gas-flow rate measuring device comprises: a second gas-flow-speed measuring circuit including a pair of bridge circuits and a differential amplifier, each of the bridge circuits consisting of four resistance elements that include a corresponding one of the two second heater elements, the differential amplifier being configured to output an output signal corresponding to a difference between output signals of the bridge circuits; and a second gas-flow-rate calculation controlling portion configured to calculate a second gas-flow-rate signal representing a flow rate of the gas passing through the airway, in accordance with a pre-stored relationship and based on the output signal outputted by the second gas-flow-speed measuring circuit. The second gas-flow-rate signal represents the direction of the gas flow through the airway in one respiratory cycle, by one peak and one trough. Thus, irrespective of the direction of the gas flow through the airway, it is possible to obtain easily understandable information indicative of the direction of the gas flow through the airway. Further, the gas-flow rate can be calculated from the output of one of the bridge circuits having the heater element located on the upstream side as viewed in the direction of the gas flow.

Preferably, in (a) an airway gas-flow rate measuring device for measuring a flow rate of a gas passing through an airway in a distal end portion of a flexible sheath, the airway gas-flow rate measuring device comprises: the above-described gas-flow sensor; (b) a first sensor substrate provided integrally or independently in a distal end portion of a gas-flow measuring catheter that passes through the flexible sheath; (c) an operating wire provided to protrude from a distal end of the first sensor substrate and to be introduced from the distal end of the first sensor substrate; (d) a diameter expansion basket constituted by a plurality of elastic wires bundled at distal and rear end portions thereof to each other, and provided in a distal end portion of the operating wire, the diameter expansion basket having a diameter that is increased when the diameter expansion basket is caused to protrude from a distal end of the gas-flow measuring catheter; a flexible first circuit substrate film wound on a portion of the operating wire which is positioned in a central portion of the diameter expansion basket in a longitudinal direction of the diameter expansion basket such that the first circuit substrate film has a cylindrical shape and is fixed to the portion of the operating wire; and the gas-flow sensor including one first heater element that is provided on an outer circumferential surface of the first circuit substrate film or two first heater elements that are provided on the outer circumferential surface of the first circuit substrate film. Owing to this arrangement, the gas-flow sensor is positioned in a central portion of the airway, thereby establishing a construction which reduces a flow resistance in the airway and which hardly causes retention of a viscous liquid in the airway and clogging of the airway, whereby the measurement of the gas-flow rate can be made accurately and easily. Particularly, the gas-flow sensor is positioned in a central portion of the diameter expansion basket in the axial direction and in the transverse cross-section of the diameter expansion basket, so that the gas-flow rate in the exhalation period can be more accurately measured.

The airway gas-flow rate measuring device, which is configured to measure the flow rate of the gas passing through the airway in the distal end portion of the flexible sheath may be used not only for a respiration flow for detecting the heartbeat signal of a living body but also for detecting, for example, a flow rate or flow speed of a gas, liquid or other fluid in a hollow organ of a living body. For such other purpose, the invention has aspects each of which is constructed as a living-body-organ fluid-flow rate measuring device as described below. That is, a first aspect of the invention is (a) a living-body-organ fluid-flow rate measuring device for measuring a flow rate of a fluid passing through an organ of a living body in a distal end portion of a flexible sheath. The living-body-organ fluid-flow rate measuring device comprises: (b) a cylindrical-shaped first sensor substrate which is integrally or independently provided in a distal end portion of a gas-flow measuring catheter that passes through the flexible sheath; (c) a flexible first circuit substrate film which is wound on an outer circumferential surface of the first sensor substrate, such that the first circuit substrate film has a cylindrical shape and is fixed to the outer circumferential surface of the first sensor substrate; (d) a gas-flow sensor including one first heater element that is provided on an outer circumferential surface of the first circuit substrate film or two first heater elements that are provided on the outer circumferential surface of the first circuit substrate film; (e) an operating wire provided to pass through the fluid-flow measuring catheter; and (f) a diameter expansion basket constituted by a plurality of elastic wires bundled at distal and rear end portions thereof to each other, and provided in a distal end portion of the operating wire, wherein the diameter expansion basket has a diameter that is increased when the diameter expansion basket is caused to protrude from a distal end of the fluid-flow measuring catheter. In the thus constructed living-body-organ fluid-flow rate measuring device, the first heater element or elements are provided on the outer circumferential surface of the flexible first circuit substrate film, which is wound on the outer circumferential surface of the first sensor substrate such that the first circuit substrate film has the cylindrical shape and is fixed to the outer circumferential surface of the first sensor substrate, and the diameter expansion basket, whose diameter is increased with the operating wire passing through the fluid measuring catheter being operatively caused to protrude, causes the first gas-flow sensor to be positioned in a center of an airway. Thus, as compared with a conventional type in which the measured gas is caused to pass between a vent hole, which is formed in a side face of a cylindrical sensor substrate that is fixed at one of its opposite ends to a catheter, and an opening of the other of the opposite ends of the cylindrical sensor substrate, it is possible to establish a construction which reduces a flow resistance in the hollow organ and which hardly causes retention of a viscous liquid in the hollow organ and clogging of the hollow organ, whereby the measurement of the gas-flow rate can be made accurately and easily.

A second aspect of the invention is (a) a living-body-organ fluid-flow rate measuring device, which includes the above-described gas-flow sensor, for measuring a flow rate of a fluid passing through an organ of a living body in a distal end portion of a flexible sheath. The living-body-organ fluid-flow rate measuring device comprises: (b) an operating wire provided to pass through the flexible sheath; (c) a diameter expansion basket constituted by a plurality of elastic wires bundled at distal and rear end portions thereof to each other, and provided in a distal end portion of the operating wire, wherein the diameter expansion basket has a diameter that is increased when the diameter expansion basket is caused to protrude from a distal end of the fluid-flow measuring catheter; (d) a second sensor substrate having a columnar shape or a cylindrical shape and provided in a distal end portion of the diameter expansion basket; (e) a flexible second circuit substrate film wound on an outer circumferential surface of the second sensor substrate such that the second circuit substrate film has a cylindrical shape and is fixed to the outer circumferential surface of the second sensor substrate; and (f) a gas-flow sensor including one second heater element that is provided on an outer circumferential surface of the second circuit substrate film or two second heater elements that are provided on the outer circumferential surface of the second circuit substrate film. In the thus constructed living-body-organ fluid-flow rate measuring device, the second heater element or elements are provided on the outer circumferential surface of the flexible second circuit substrate film, which is wound on the outer circumferential surface of the second sensor substrate such that the second circuit substrate film has the cylindrical shape and is fixed to the outer circumferential surface of the second sensor substrate, and the diameter expansion basket, whose diameter is increased with the operating wire passing through the flexible sheath being operatively caused to protrude, causes the second gas-flow sensor to be positioned in a center of an airway. Thus, as compared with a conventional type in which the measured gas is caused to pass between a vent hole, which is formed in a side face of a cylindrical sensor substrate that is fixed at one of its opposite ends to a catheter, and an opening of the other of the opposite ends of the cylindrical sensor substrate, it is possible to establish a construction which reduces a flow resistance in the hollow organ and which hardly causes retention of a viscous liquid in the hollow organ and clogging of the hollow organ, whereby the measurement of the gas-flow rate can be made accurately and easily.

A third aspect of the invention is (a) a living-body-organ fluid-flow rate measuring device for measuring a flow rate of a gas passing through an organ of a living body in a distal end portion of a flexible sheath. The living-body-organ fluid-flow rate measuring device comprises: (b) a cylindrical-shaped first sensor substrate which is integrally or independently provided in a distal end portion of the flexible sheath; (c) a flexible first circuit substrate film which is wound on an outer circumferential surface of the first sensor substrate, such that the first circuit substrate film has a cylindrical shape and is fixed to the outer circumferential surface of the first sensor substrate; (d) a first gas-flow sensor including one first heater element that is provided on an outer circumferential surface of the first circuit substrate film or two first heater elements that are provided on the outer circumferential surface of the first circuit substrate film; an operating wire provided to pass through the fluid-flow measuring catheter; (e) a diameter expansion basket constituted by a plurality of elastic wires bundled at distal and rear end portions thereof to each other, and provided in a distal end portion of the operating wire, wherein the diameter expansion basket has a diameter that is increased when the diameter expansion basket is caused to protrude from a distal end of the fluid-flow measuring catheter; (f) a second sensor substrate having a columnar shape or a cylindrical shape and provided in a distal end portion of the diameter expansion basket; (g) a flexible second circuit substrate film wound on an outer circumferential surface of the second sensor substrate such that the second circuit substrate film is fixed to the outer circumferential surface of the second sensor substrate; and (h) a second gas-flow sensor including one second heater element that is provided on an outer circumferential surface of the second circuit substrate film or two second heater elements that are provided on the outer circumferential surface of the second circuit substrate film. In the thus constructed living-body-organ fluid-flow rate measuring device, the first heater element or elements are provided on the outer circumferential surface of the flexible first circuit substrate film, which is wound on the outer circumferential surface of the first sensor substrate such that the first circuit substrate film has the cylindrical shape and is fixed to the outer circumferential surface of the first sensor substrate, while the second heater element or elements are provided on the outer circumferential surface of the flexible second circuit substrate film, which is wound on the outer circumferential surface of the second sensor substrate such that the second circuit substrate film has the cylindrical shape and is fixed to the outer circumferential surface of the second sensor substrate. Further, the diameter expansion basket, whose diameter is increased with the operating wire passing through the fluid measuring catheter being operatively caused to protrude, causes the first and second gas-flow sensors to be positioned in a center of the airway. Thus, as compared with a conventional type in which the measured gas is caused to pass between a vent hole, which is formed in a side face of a cylindrical sensor substrate that is fixed at one of its opposite ends to a catheter, and an opening of the other of the opposite ends of the cylindrical sensor substrate, it is possible to establish a construction which reduces a flow resistance in the hollow organ and which hardly causes retention of a viscous liquid in the hollow organ and clogging of the hollow organ, whereby the measurement of the gas-flow rate can be made accurately and easily. Further, since the first and second gas-flow sensors are provided on respective opposite sides of the diameter expansion basket in the hollow organ, it is possible to measure the flow rate by using one of the first and second heater elements which is located on an upstream side, as viewed in a direction of the gas flow, of the other in the airway, thereby enabling the flow rate to be more accurately measured by using a fluid flow which is not disturbed by the diameter expansion basket and which does not contain temperature noise caused by the upstream-side heater element.

According to a fourth aspect of the invention, in the above-described first or third aspect of the invention, the flexible first circuit substrate film is fixedly wound on the outer circumferential surface of the first sensor substrate via a spacer, such that a space is defined between an outer circumferential surface of the first sensor substrate and at least a portion or portions of the first circuit substrate film in which the one or two first heater elements are provided. Owing to this arrangement, the first sensor substrate is thermally insulated from the first heater element or elements provided on the first circuit substrate film by an increased degree, whereby the gas-flow rate can be more accurately measured. Further, the responsiveness with respect to the heat is dependent on a heat capacity of the first heater element or elements themselves, thereby making it possible to obtain a high-speed response.

According to a fifth aspect of the invention, in the above-described second or third aspect of the invention, the flexible second circuit substrate film is fixedly wound on the outer circumferential surface of the second sensor substrate via a spacer, such that a space is defined between an outer circumferential surface of the second sensor substrate and at least a portion or portions of the second circuit substrate film in which the one or two heater elements are provided. Owing to this arrangement, the second sensor substrate is thermally insulated from the second heater element or elements provided on the second circuit substrate film by an increased degree, whereby the gas-flow rate can be more accurately measured. Further, the responsiveness with respect to the heat is dependent on a heat capacity of the second heater element or elements themselves, thereby making it possible to obtain a high-speed response.

According to a sixth aspect of the invention, in the above-described first, third or fourth aspect of the invention, the first circuit substrate film is provided with the two first heater elements as a pair of first heater elements formed thereon. Further, the airway gas-flow rate measuring device comprises: a first gas-flow-speed measuring circuit including a pair of bridge circuits and a differential amplifier, each of the bridge circuits consisting of four resistance elements that include a corresponding one of the two first heater elements, the differential amplifier being configured to output an output signal corresponding to a difference between output signals of the bridge circuits; and a first gas-flow-rate calculation controlling portion configured to calculate a first gas-flow-rate signal representing a flow rate of the gas passing through the airway, in accordance with a pre-stored relationship and based on the output signal outputted by the first gas-flow-speed measuring circuit. The first gas-flow rate signal represents the direction of the gas flow through the airway in one respiratory cycle, by one peak and one trough. Thus, irrespective of the direction of the gas flow through the airway, it is possible to obtain easily understandable information indicative of the direction of the gas flow through the airway. Further, the gas-flow rate can be calculated from the output of one of the bridge circuits having the heater element located on the upstream side as viewed in the direction of the gas flow.

According to a seventh aspect of the invention, in the above-described third or fifth aspect of the invention, the second circuit substrate film is provided with the two second heater elements as a pair of second heater elements formed thereon. Further, the airway gas-flow rate measuring device comprises: a second gas-flow-speed measuring circuit including a pair of bridge circuits and a differential amplifier, each of the bridge circuits consisting of four resistance elements that include a corresponding one of the two second heater elements, the differential amplifier being configured to output an output signal corresponding to a difference between output signals of the bridge circuits; and a second gas-flow-rate calculation controlling portion configured to calculate a second gas-flow-rate signal representing a flow rate of the gas passing through the airway, in accordance with a pre-stored relationship and based on the output signal outputted by the second gas-flow-speed measuring circuit. The second gas-flow-rate signal represents the direction of the gas flow through the airway in one respiratory cycle, by one peak and one trough. Thus, irrespective of the direction of the gas flow through the airway, it is possible to obtain easily understandable information indicative of the direction of the gas flow through the airway. Further, the gas-flow rate can be calculated from the output of one of the bridge circuits having the heater element located on the upstream side as viewed in the direction of the gas flow.

An eighth aspect of the invention is, in (a) an airway gas-flow rate measuring device for measuring a flow rate of a gas passing through an airway in a distal end portion of a flexible sheath, the airway gas-flow rate measuring device comprises: the above-described gas-flow sensor; (b) a first sensor substrate provided integrally or independently in a distal end portion of a gas-flow measuring catheter that passes through the flexible sheath; (c) an operating wire provided to protrude from a distal end of the first sensor substrate and to be introduced from the distal end of the first sensor substrate; (d) a diameter expansion basket constituted by a plurality of elastic wires bundled at distal and rear end portions thereof to each other, and provided in a distal end portion of the operating wire, the diameter expansion basket having a diameter that is increased when the diameter expansion basket is caused to protrude from a distal end of the gas-flow measuring catheter; a flexible first circuit substrate film wound on a portion of the operating wire which is positioned in a central portion of the diameter expansion basket in a longitudinal direction of the diameter expansion basket such that the first circuit substrate film has a cylindrical shape and is fixed to the portion of the operating wire; and the gas-flow sensor including one first heater element that is provided on an outer circumferential surface of the first circuit substrate film or two first heater elements that are provided on the outer circumferential surface of the first circuit substrate film. Owing to this arrangement, the gas-flow sensor is positioned in a central portion of the airway, thereby establishing a construction which reduces a flow resistance in the airway and which hardly causes retention of a viscous liquid in the airway and clogging of the airway, whereby the measurement of the gas-flow rate can be made accurately and easily. Particularly, the gas-flow sensor is positioned in a central portion of the diameter expansion basket in the axial direction and in the transverse cross-section of the diameter expansion basket, so that the gas-flow rate can be more accurately measured.

MODES FOR CARRYING OUT THE INVENTION

Hereinafter, a heartbeat-signal detecting device according to an embodiment of the present invention will be described in detail with reference to the drawings.

Embodiment 1

Figure 1:
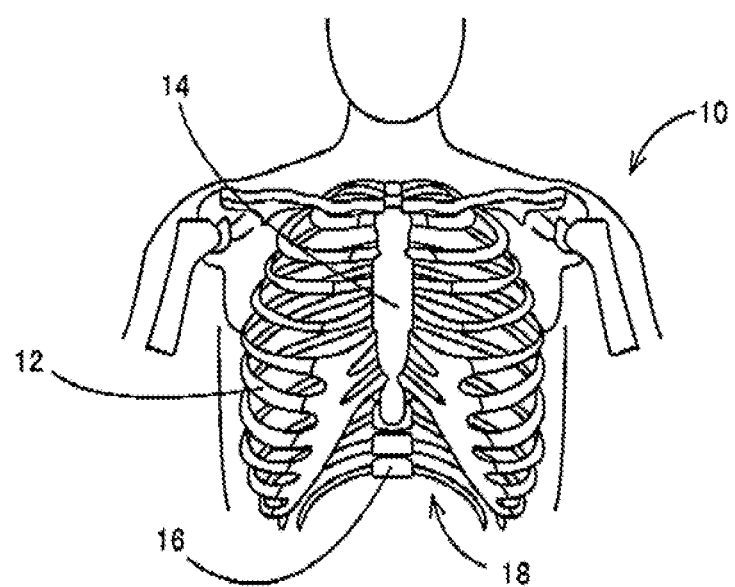
FIG. 1 is a schematic view explaining a thorax of a living body.
Figure 2:
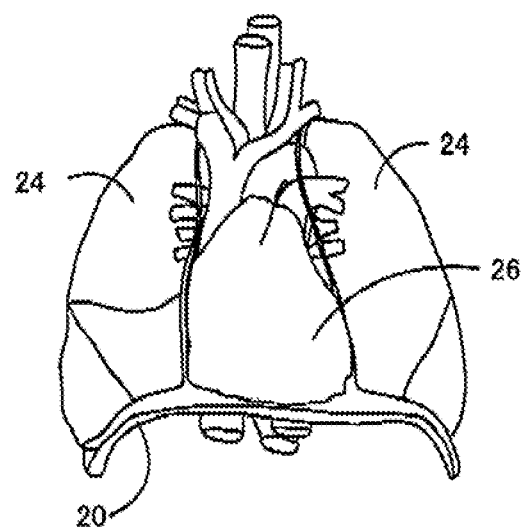
FIG. 2 is a schematic view showing lungs and a heart accommodated in the thorax of FIG. 1.

As shown in FIGS. 1 and 2, in a living body 10, there are accommodated lungs 24 and a heart 26 within a thoracic cavity that is isolated by a thorax 18 having a relatively high rigidity and a thoracic diaphragm 20 closing a lower opening of the thorax 18, wherein the thorax 18 is surrounded by ribs 12, a sternum 14 and thoracic vertebrae 16. Although a volumetric change of the heart 26, which is caused by a pulse, is smaller than a volumetric change of the lungs 24, which is caused by a respiratory motion, the cycle of the volumetric change of the heart 26 is short so that the volumetric change of the heart 26 is clearly superimposed on the ventilatory waveform of the lungs 24. Therefore, attention was paid to a point that, if a respiratory waveform (ventilatory waveform), which represents a flow speed or flow rate of a gas passing through a trachea 28 of the living body 10, is detected, a heartbeat signal can be extracted from the detected respiratory waveform. Hereinafter, it will be described in detail.

Figure 3:
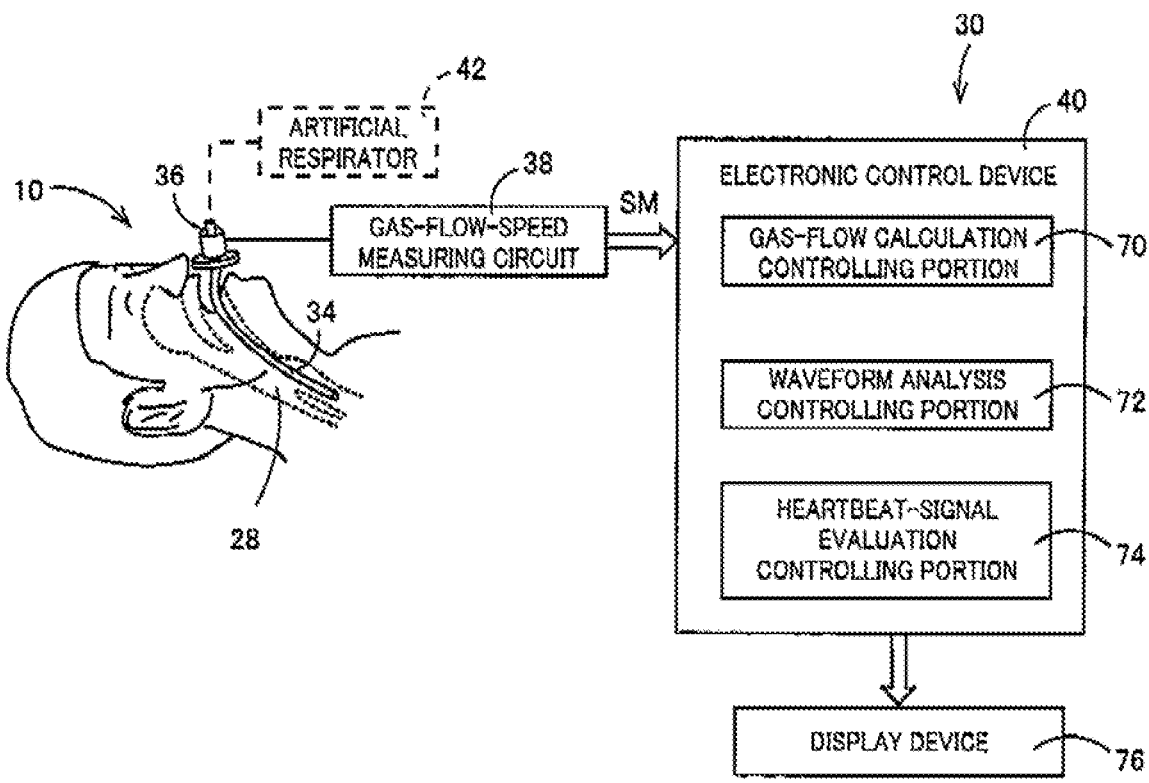
FIG. 3 is a view explaining a construction of a heartbeat-signal detecting device according to an embodiment of the invention and also a main portion of a control function of an electronic control device that is included in the heartbeat-signal detecting device.

FIG. 3 is a view explaining a construction of a heartbeat-signal detecting device 30 according to an embodiment of the present invention and also a function of an electronic control device 40 that is provided in the heartbeat-signal detecting device 30. The heartbeat-signal detecting device 30 includes: a gas-flow sensor 36 provided in an endotracheal intubation tube 34 that is inserted into the trachea 28 of the living body 10; a gas-flow-speed measuring circuit 38 configured to output a measurement signal SM corresponding to a flow rate of a gas passing through the gas-flow sensor 36, based on a signal supplied from the gas-flow sensor 36; an electronic control device 40 configured to extract, from the measurement signal SM outputted by the gas-flow-speed measuring circuit 38, the heartbeat signal SH representing the volumetric change of the heart 26; and a display device 76 configured to display, for example, evaluations of the heart rate, the waveform of the heartbeat signal SH, the respiratory waveform and the heartbeat waveform, which are results of signal processing made by the electronic control device 40.

Figure 4:
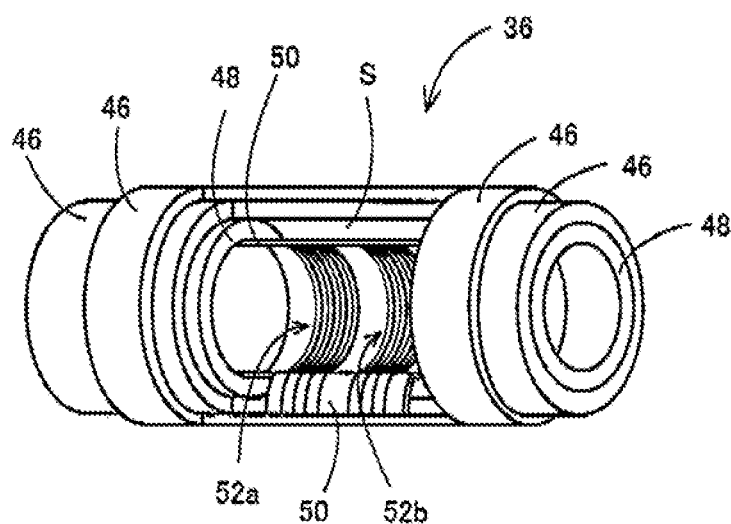
FIG. 4 is a perspective view showing a mechanical construction of a gas-flow sensor used in FIG. 3.
Figure 5:
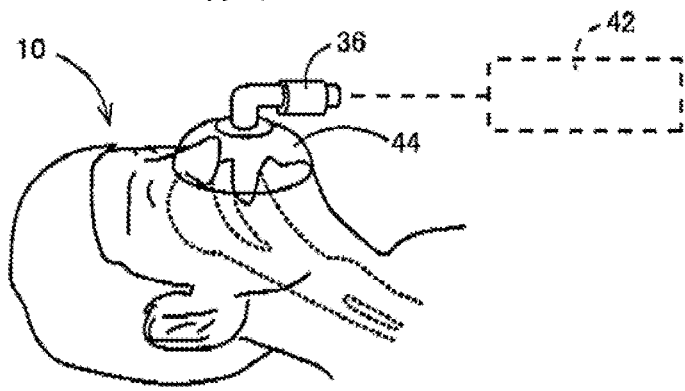
FIG. 5 is a perspective view showing, by way of example, the gas-flow sensor of FIG. 4 which is provided to cover a nose and a mouth of a living body.

FIG. 4 is a perspective view showing a mechanical construction of the gas-flow sensor 36, by way of example. Although the gas-flow sensor 36 is provided in a proximal end portion of the endotracheal intubation tube 34 in an example shown in FIG. 3, the gas-flow sensor 36 may be provided in an intermediate portion or exit portion of the endotracheal intubation tube 34, or in a flexible tube or connection adaptor interconnecting between the endotracheal intubation tube 34 and an artificial respirator 42, or in any other portion that enables the gas-flow sensor 36 to detect a flow rate of a gas passing through the trachea 28 of the living body 10. Further, as shown in FIG. 5, the gas-flow sensor 36 may be provided in a mask 44 covering a nose and a mouth of the living body 10 or in a flexible tube or connection adaptor interconnecting between the mask 44 and the artificial respirator 42. The artificial respirator 42 shown in FIGS. 3 and 5 is provided as needed, and does not necessarily have to be provided.

As shown in the perspective view of FIG. 4, the gas-flow sensor 36: includes a two-layered tubular case 46 connectable to the endotracheal intubation tube 34 and the artificial respirator 42; a pair of tubular spacers 48 disposed in the tubular case 46 so as to be spaced apart from each other by a predetermined space in a direction of an axis of the tubular case 46; a circuit substrate film 50 mounted or fixed onto inner circumferential surfaces of the respective tubular spacers 48 and made of parylene resin, epoxy resin, polyimide resin or other electrically insulated material having flexibility; and a pair of heater elements 52a, 52b provided on an inner circumferential surface of the circuit substrate film 50 by photolithography and made of platinum resistance element, gold resistance element or other electric resistance element whose electric resistance is changed depending on temperature. The circuit substrate film 50, which is fixed onto the pair of tubular spacers 48, has an intermediate portion, as viewed in the direction of the axis, which extends along an inner wall surface of the tubular case 46 and is spaced apart from the inner wall surface by a predetermined space S. The pair of heater elements 52a, 52b, which are provided on the inner circumferential surface of the circuit substrate film 50, are located inside opposite ends of the circuit substrate film 50 in the direction of the axis. The gas-flow sensor 36 is configured to detect the flow rate of the gas passing through the tubular case 46, based on the electric resistance of the heater elements 52a, 52b heated by electricity supplied thereto, which is changed depending on the flow rate of the gas passing through the tubular case 46.

Figure 6:
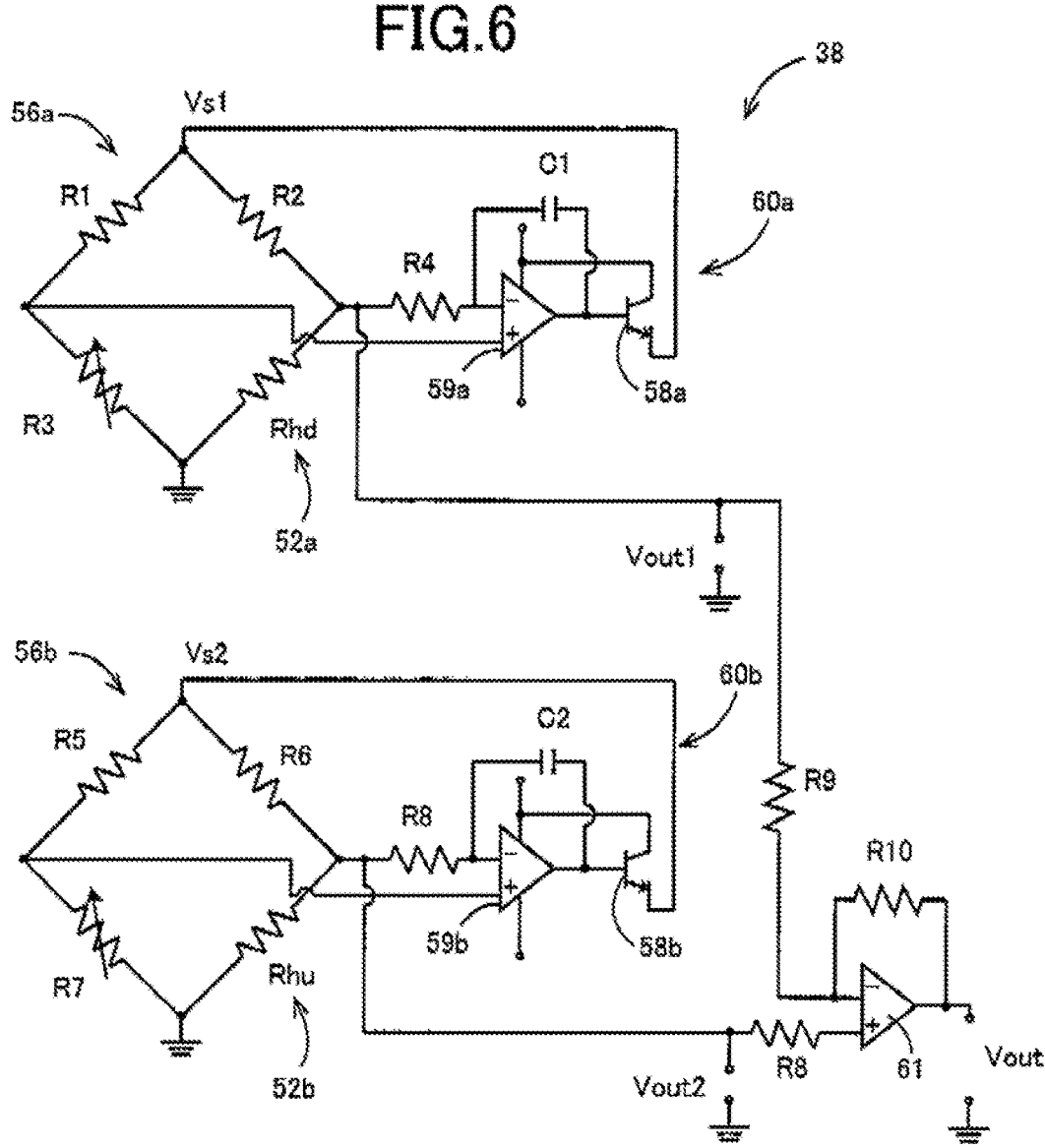
FIG. 6 is a circuit diagram explaining a construction of a gas-flow rate electric circuit for operating the gas-flow sensor of FIG. 4.

FIG. 6 shows a constant-temperature-type measuring circuit as a construction of the gas-flow-speed measuring circuit 38 by way of example. As shown in FIG. 6, the gas-flow-speed measuring circuit 38 includes a first bridge circuit 56a and a first measuring circuit 60a, wherein the first bridge circuit 56a is constituted by four resistors, i.e., resistors R1, R2, R3 and the heater element 52a (resistance value Rhd), and a first bridge power-supply voltage Vs1 is applied to the first bridge circuit 56a, and wherein the first measuring circuit 60a includes a first feedback amplifier 59a configured to amplify an output voltage Vout1 of the first bridge circuit 56a and a first transistor 58a configured to supply an electric current corresponding to a signal representing the output voltage Vout1, to the first bridge circuit 56a. The gas-flow-speed measuring circuit 38 further includes a second bridge circuit 56b and a second measuring circuit 60b, wherein the second bridge circuit 56b is constituted by four resistors, i.e., resistors R5, R6, R7 and the heater element 52b (resistance value Rhu), and a second bridge power-supply voltage Vs2 is applied to the second bridge circuit 56b, and wherein the second measuring circuit 60b includes a second feedback amplifier 59b configured to amplify an output voltage Vout2 of the second bridge circuit 56b and a second transistor 58b configured to supply an electric current corresponding to a signal representing the output voltage Vout2, to the second bridge circuit 56b. The above-descried output voltage Vout1 and output voltage Vout2 represent the gas flow speed. The gas-flow-speed measuring circuit 38 still further includes a differential amplifier 61 configured to amplify a difference voltage between the output voltage Vout1 of the first bridge circuit 56a and the output voltage Vout2 of the second bridge circuit 56b, and then to output an output voltage Vout. The above-described resistor R3 is a variable resistor configured to adjust an equilibrium state of the first bridge circuit 56a. The above-described resistor R7 is a variable resistor configured to adjust an equilibrium state of the second bridge circuit 56b.

In the gas-flow-speed measuring circuit 38 constructed as described above, when the gas flow speed is suddenly increased from the equilibrium state in the first bridge circuit 56a, the temperature of the first heater element 52a is reduced whereby the resistance value Rhd is reduced. In this instance, for restoring the equilibrium state of the first bridge circuit 56a, the first bridge power-supply voltage Vs1 is increased by the first feedback amplifier 59a whereby the temperature of the first heater element 52a is increased and is held in a constant temperature. Similarly, when the gas flow speed is suddenly increased from the equilibrium state in the second bridge circuit 56b, the temperature of the second heater element 52b is reduced whereby the resistance value Rhu is reduced. In this instance, for restoring the equilibrium state of the second bridge circuit 56b, the second bridge power-supply voltage Vs2 is increased by the feedback amplifier 59b whereby the temperature of the second heater element 52b is increased and is held in a constant temperature. In the gas-flow-speed measuring circuit 38, the output voltage Vout, which is outputted from the differential amplifier 61 and which represents the difference voltage between the output voltage Vout1 of the first bridge circuit 56a and the output voltage Vout2 of the second bridge circuit 56b, constitutes a signal reflecting a difference between resistance changes in the respective heater elements 52a, 52b, namely, forms a waveform representing a forward direction or reverse direction as the direction of the gas flow through the trachea 28. That is, the output voltage Vout constitutes a signal representing the direction of the gas flow, by a waveform consisting of one peak and one trough in one respiratory cycle.

Figure 7:
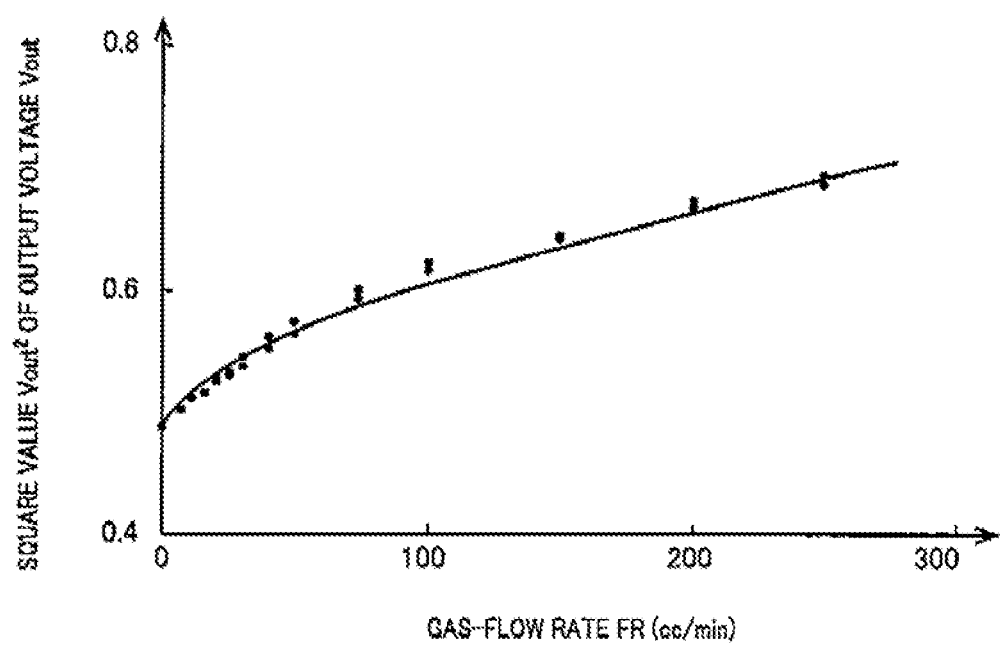
FIG. 7 is a view explaining a relationship which is pre-stored in a flow-rate calculation controlling portion in the electronic control device of FIG. 3 and which is between an output voltage of the gas-flow-speed measuring circuit and a flow rate of a gas having passed through the gas-flow sensor.

The flow rate FR (cc/min) is calculated in accordance with, for example, a pre-obtained calibration curve shown in FIG. 7, i.e., a relationship between the flow rate FR (cc/min) and a square value of an output voltage, and based on one of the output voltage Vout1 and output voltage Vout2 that are outputted from the respective first and second bridge circuits 56a, 56b containing the respective heater elements 52a, 52b, wherein the one of the output voltage Vout1 and output voltage Vout2 is outputted from one of the bridge circuits 56a, 56b whose heater element is located on an upstream side. The above-described one of the output voltage Vout1 and output voltage Vout2 is selected depending on whether the output voltage Vout of the gas-flow-speed measuring circuit 38 is positive or negative. The flow rate FR (cc/min) of the gas flowing through the gas-flow sensor 36 is obtained, by multiplying the output voltage Vout1 or output voltage Vout2 outputted from the gas-flow-speed measuring circuit 38 and representing the flow speed FS (cm/sec), with a pre-obtained flow cross-sectional area C (constant) of the gas-flow sensor 36. It is noted that the flow speed FS (cm/sec) may be used for the abscissa in the relationship shown in FIG. 7, in place of the gas-flow rate.

Referring back to FIG. 3, the electronic control device 40 is constituted by a so-called microcomputer of type in which programs pre-stored in ROM or RAM are to be executed by CPU. The electronic control device 40 functions as control function means, which includes a gas-flow calculation controlling portion 70, a waveform analysis controlling portion 72 and a heartbeat-signal evaluation controlling portion 74. The electronic control device 40 causes the display device 76 to display, for example, evaluations of the heart rate, the waveform of the heartbeat signal SH, the respiratory waveform and the heartbeat waveform, which are results of the signal processing.

Figure 8:
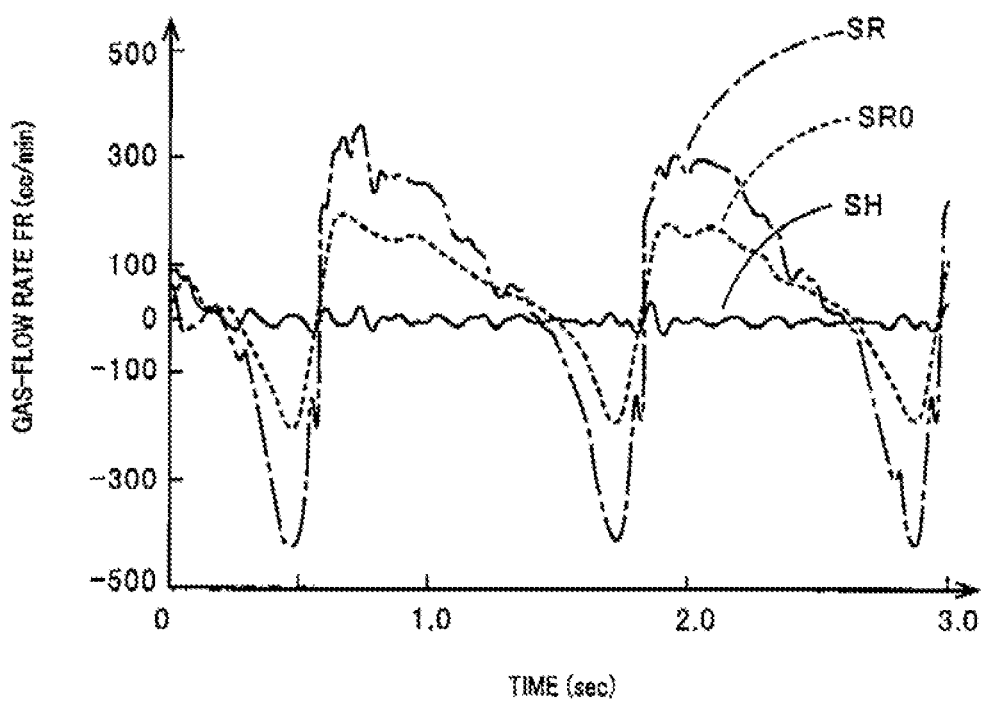
FIG. 8 is a view showing a respiration signal SR, a ventilation component signal SR0 and a heartbeat signal SH that were detected at the same time from a living body, wherein the ventilation component signal SR0 represents a lung capacity component originating from a thorax and a thoracic diaphragm of the living body.

The gas-flow calculation controlling portion 70 calculates the flow rate FR (cc/min) or flow speed FS (cm/sec) in accordance with the pre-stored relationship shown in FIG. 7, which is a relationship between the flow rate FR (cc/min) or flow speed FS (cm/sec) of the gas passing through the gas-flow sensor 36 and the square value $Vout^2$ of the output voltage Vout of the gas-flow-speed measuring circuit 38, wherein the output voltage Vout is outputted as a gas flow speed signal from the gas-flow-speed measuring circuit 38. The gas-flow calculation controlling portion 70 outputs an waveform representing change of the calculated flow rate FR or flow speed FS, i.e., a respiration signal SR representing a lung capacity reflecting the respiratory motion. The respiration signal SR shown in FIG. 8 represents a cyclic change of the flow rate FR that is in synchronization with respiration, i.e., the respiratory waveform of the lungs 24 of the living body.

Figure 9:
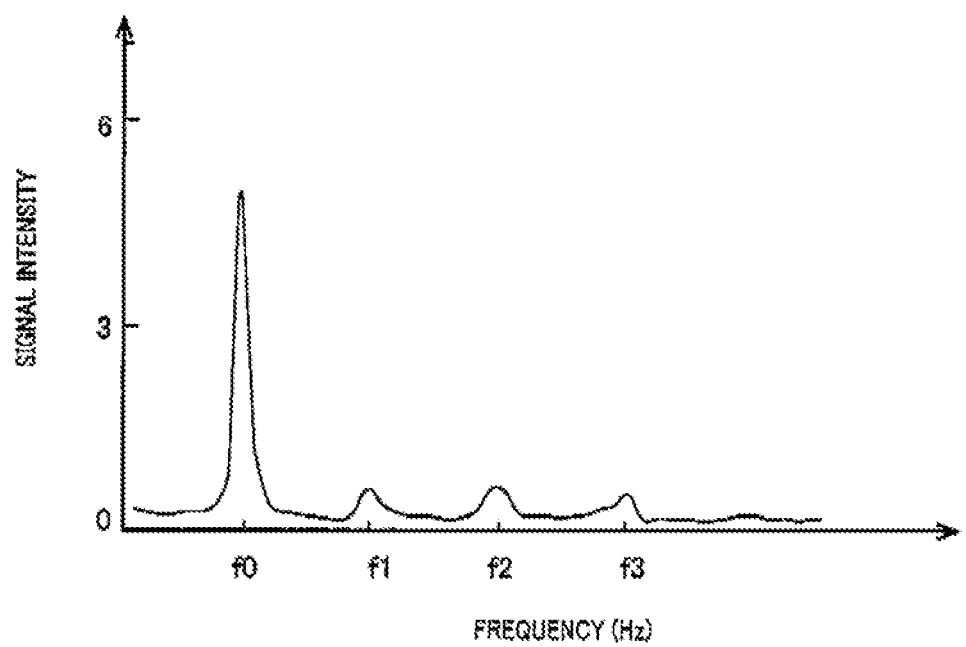
FIG. 9 is a view showing a frequency spectrum of the heartbeat signal SH and frequency components of the heartbeat signal SH.
Figure 10:
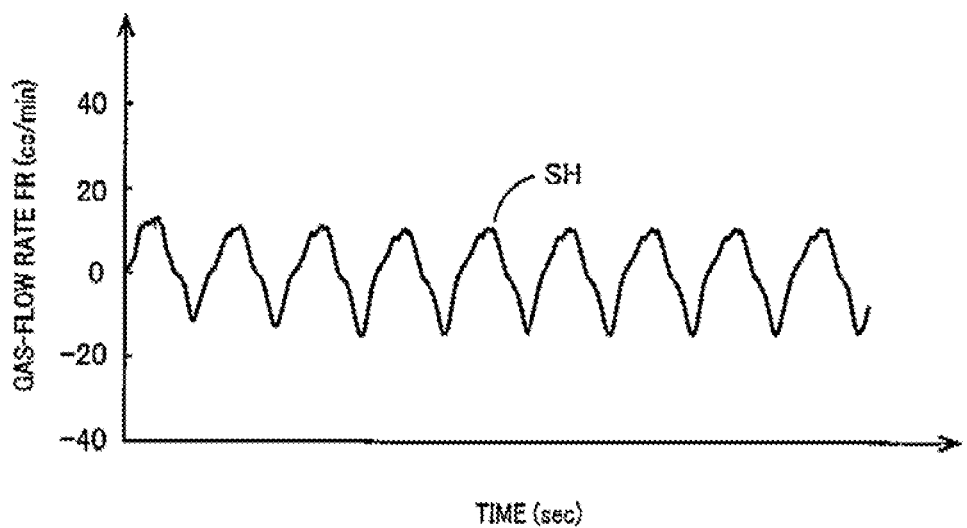
FIG. 10 is a view showing the heartbeat signal SH, which was composed from the frequency components constituting the heartbeat signal by means of inverse Fourier transform, together with a measured wave, in an overlapped manner.

The waveform analysis controlling portion 72 extracts, from the respiration signal SR on which the heartbeat waveform is superimposed, the heartbeat signal SH representing the heartbeat waveform, based on frequency characteristics of the heartbeat waveform that has a fundamental frequency higher than that of the respiratory waveform represented by the respiration signal SR. The waveform analysis controlling portion 72 makes a frequency analysis of a waveform represented by the heartbeat signal SH that is superimposed on the respiration signal SR in synchronization with pulse of the heart 26, by means of Fourier transform, so as to pre-obtain a fundamental frequency f0, a first harmonic f1, a second harmonic f2 and a third harmonic f3 as frequency components of the heartbeat signal SH that are presented in a frequency spectrum of the heartbeat signal SH as shown in FIG. 9. Then, the waveform analysis controlling portion 72 composes the heartbeat signal SH from the frequency components by means of inverse Fourier transform, as shown in FIG. 10. The heartbeat signal SH superimposed on the respiration signal SR is collected, for example, by ECG waveform as a trigger. In FIG. 10, the thus estimated heartbeat signal SH and an actually measured waveform are represented to overlap with each other, and are well coincident with each other. It is noted that the waveforms of FIGS. 9 and 10 were obtained from a rat.

The waveform analysis controlling portion 72 removes, from the respiration signal SR outputted from the gas-flow sensor 36, the heartbeat signal SH, i.e., frequency components which are in synchronization with the pulse of the heart 26 of the living body 10 superimposed on the respiration signal SR, and outputs a ventilation component signal SR0 representing a lung capacity component originating from the thorax 18 and the thoracic diaphragm 20 of the living body 10. The waveform analysis controlling portion 72 causes the respiration signal SR to pass through a low pass filter or band pass filter that allows passage of frequencies lower than frequency components constituting the heartbeat signal SH, so as to output the ventilation component signal SR0 shown in FIG. 8, which represents the lung capacity component originating from the thorax 18 and the thoracic diaphragm 20 of the living body 10 and on which the respiration heartbeat signal SH is not superimposed. Or alternatively, the waveform analysis controlling portion 72 outputs the ventilation component signal SR0 which represents the lung capacity component originating from the thorax 18 and the thoracic diaphragm 20 of the living body 10 and on which the respiration heartbeat signal SH is not superimposed, by extracting frequency components constituting a frequency spectrum of the respiration signal SR from the frequency spectrum of the respiration signal SR outputted from the gas-flow sensor 36 and then obtaining the ventilation component signal SR0 from the extracted frequency components by means of inverse Fourier transform.

Figure 11:
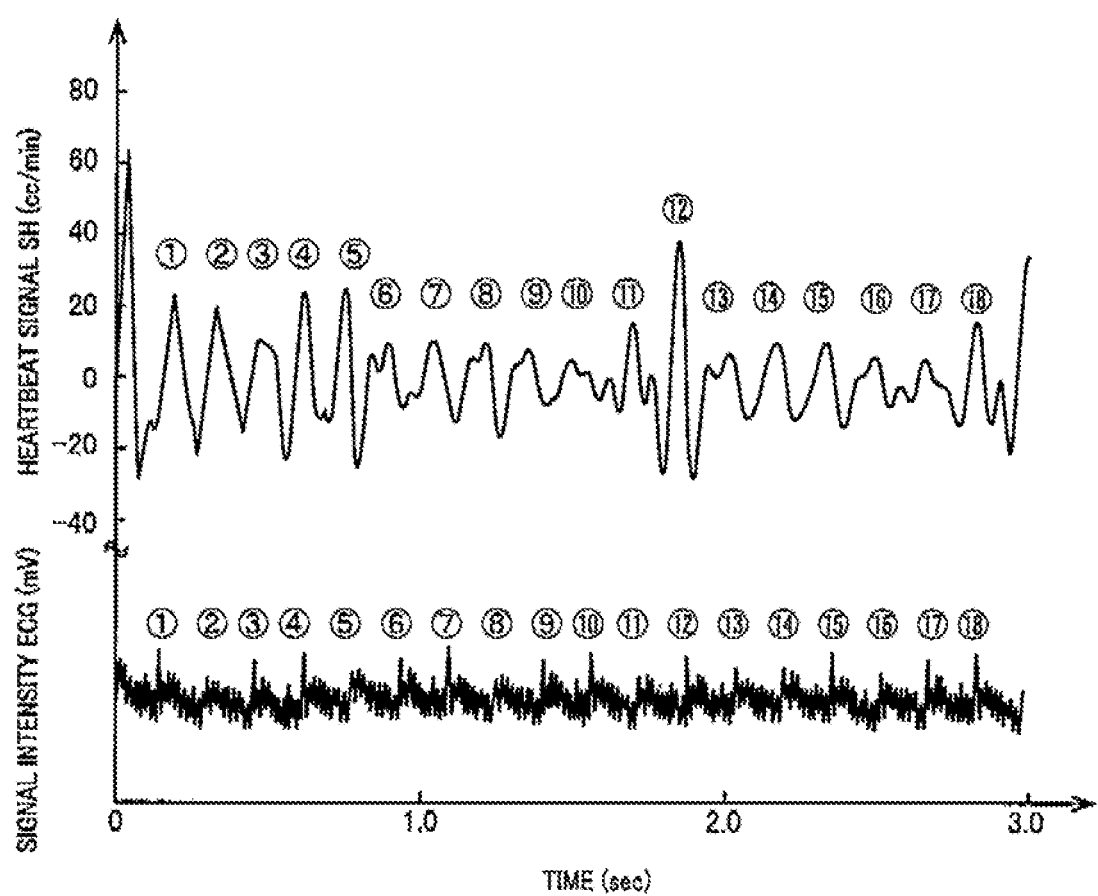
FIG. 11 is a view showing the heartbeat signal SH and an electrocardiogram that were obtained at the same time, in a comparative manner.

The heartbeat-signal evaluation controlling portion 74 calculates the heart rate HR of the living body 10 from a generation cycle of the heartbeat signal SH, and makes an abnormality determination in a case when the calculated heart rate HR is deviated from an upper limit or lower limit of a predetermined reference range. In this case, the heartbeat-signal evaluation controlling portion 74 causes the display device 76 to output an abnormality of the heart rate HR through a display of the display device 76. The heartbeat-signal evaluation controlling portion 74 calculates an amplitude value A of the heartbeat signal SH, and makes an abnormality determination in a case when the calculated amplitude value A is deviated from an upper limit or lower limit of a predetermined reference range. In this case, the heartbeat-signal evaluation controlling portion 74 causes the display device 76 to output an abnormality of the amplitude value A through the display of the display device 76. Thus, it is possible to evaluate not only a drug effect of a circulatory system drug having a chronotropic effect that changes a heart rate but also a drug effect of a circulatory system drug having an inotropic effect that changes a cardiac output. Particularly, the capability of making the evaluation of the drug effect of a circulatory system drug having an inotropic effect that changes a cardiac output is advantageous because such an evaluation cannot be made by ECG (electrocardiogram). FIG. 11 is a view for comparing the heartbeat signal SH and ECG simultaneously obtained from a rat, and shows that circled numbers 1-18 denoting peaks of the heartbeat signal SH presented in the upper section are well coincident with circled numbers 1-18 denoting R-waves of the ECG presented in the lower section.

The heartbeat-signal evaluation controlling portion 74 evaluates a functional abnormality or an anatomic abnormality of two atria and two ventricles constituting the heart 26, based on the heartbeat signal SH analyzed by the waveform analysis controlling portion 72, and causes the display device 76 to output an indication indicative of the abnormal state through the display of the display device 76. The heartbeat-signal evaluation controlling portion 74 calculates, for example, a correlation coefficient C between the heartbeat waveform represented by the heartbeat signal SH calculated by the waveform analysis controlling portion 72 and pre-stored plurality of kinds of abnormality evaluation patterns. The heartbeat-signal evaluation controlling portion 74 determines the functional abnormality or anatomic abnormality of two atria and two ventricles constituting the heart 26, which is indicated by the abnormality evaluation pattern in which the correlation coefficient C exceeds a predetermined determination value, and then evaluates a degree of the abnormality. The heartbeat waveform indicated by the heartbeat signal SH represents a sum total of capacity changes of the two atria and two ventricles constituting the heart 26, so that the heartbeat waveform reflects the functional abnormality or anatomic abnormality of any one of the two atria and two ventricles that are different from one another in terms of timing of the volumetric change. Further, under an artificial respiration management, particularly, in a situation where a positive end expiratory pressure (PEEP) is employed to prevent an alveolar collapse and improve a lung oxygenation by applying a pressure higher than an atmospheric pressure at an end-tidal stage, it is considered that pressure of alveoli limits an expansion of volume of the heart 26 that is adjacent to the alveoli and affects a hemodynamics. The abnormality in which the expansion of the heart 26 is limited is evaluated based on the correlation coefficient between the abnormality evaluation pattern reflecting such a situation and the heartbeat waveform represented by the heartbeat signal SH.

Figure 12:
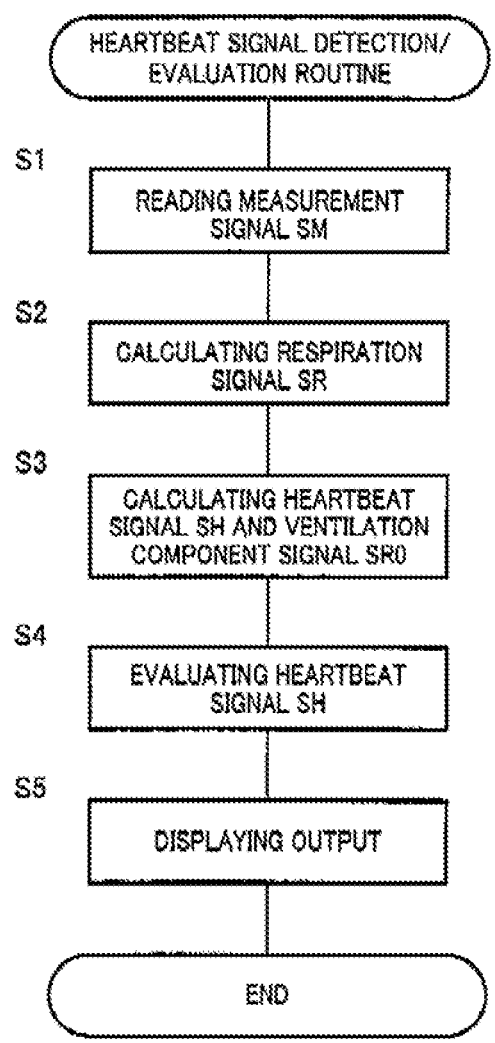
FIG. 12 is a flow chart indicting a main portion of a control operation of the electronic control device of FIG. 3.

FIG. 12 is a flow chart for explaining a main portion of a control operation of the electronic control device 40, i.e., execution of a heartbeat signal detection/evaluation routine. At step S1 (hereinafter "step" is omitted) corresponding to the flow-rate calculation controlling portion, the measurement signal SM corresponding to the output voltage Vout of the gas-flow-speed measuring circuit 38, i.e., the flow speed of the gas passing through the gas-flow sensor 36 is read during a length of time corresponding to at least one respiratory cycle of the living body 10. Next, at S2 corresponding to the gas-flow calculation controlling portion 70, the flow rate FR is calculated in accordance with, for example, the pre-stored relationship shown in FIG. 7, which is a relationship between the flow rate FR (cc/min) of the gas passing through the gas-flow sensor 36 and the square value $Vout^2$ of the output voltage Vout of the gas-flow-speed measuring circuit 38, based on the square value $Vout^2$ of the output voltage Vout of the gas-flow-speed measuring circuit 38 reflecting an actual gas flow speed of the gas passing through the gas-flow sensor 36. Further, the respiration signal SR representing the waveform of change of the flow rate FR, i.e., the respiratory waveform of FIG. 8, is calculated. Next, at S3 corresponding to the waveform analysis controlling portion 72, the heartbeat signal SH representing the heartbeat waveform is extracted from the respiration signal SR on which the heartbeat waveform is superimposed, based on the frequency characteristics of the heartbeat waveform having a fundamental frequency higher than that of the respiration signal SR. For example, a frequency analysis of a waveform represented by the heartbeat signal SH that is superimposed on the respiration signal SR in synchronization with pulse of the heart 26, is made by means of Fourier transform, so as to pre-obtain the fundamental frequency f0, first harmonic f1, second harmonic f2 and third harmonic f3 as frequency components of the heartbeat signal SH that are presented in the frequency spectrum of the heartbeat signal SH as shown in FIG. 9. Then, the heartbeat signal SH is composed from the frequency components by means of inverse Fourier transform, as shown in FIG. 10. The heartbeat signal SH superimposed on the respiration signal SR is collected, for example, by ECG waveform as a trigger. In FIG. 10, the thus estimated heartbeat signal SH and an actually measured waveform are represented to overlap with each other, and are well coincident with each other. It is noted that the waveforms of FIGS. 9 and 10 were obtained from a rat. Further, the heartbeat signal SH, i.e., frequency components which are in synchronization with the pulse of the heart 26 of the living body 10 superimposed on the respiration signal SR, is removed from the respiration signal SR outputted from the gas-flow sensor 36, and the ventilation component signal SR0, which represents the respiratory waveform indicating only change of the flow rate FR corresponding to volumetric change of the lungs 24 of the living body 10, is calculated. The calculated ventilation component signal SR0 represents also the lung capacity component which originates from the thorax 18 and the thoracic diaphragm 20 of the living body 10 and on which the respiration heartbeat signal SH is not superimposed. Then, the respiration signal SR is caused to pass through, for example, a low pass filter or band pass filter that allows passage of frequencies lower than frequency components constituting the heartbeat signal SH, so as to remove the heartbeat signal SH from the respiration signal SR, for thereby calculating the ventilation component signal SR0 shown in FIG. 8, which represents the lung capacity component originating from the thorax 18 and the thoracic diaphragm 20 of the living body 10 and on which the respiration heartbeat signal SH is not superimposed. Or alternatively, the ventilation component signal SR0, which represents the lung capacity component originating from the thorax 18 and the thoracic diaphragm 20 of the living body 10 and on which the respiration heartbeat signal SH is not superimposed, is calculated by extracting frequency components constituting the respiration signal SR, from a frequency spectrum of the respiration signal SR outputted from the gas-flow sensor 36 and then obtaining the ventilation component signal SR0 from the extracted frequency components by means of inverse Fourier transform.

Next, at S4 corresponding to the heartbeat-signal evaluation controlling portion 74, the heart rate HR of the living body 10 is calculated from a generation cycle of the heartbeat signal SH, and an abnormality determination is made in a case when the calculated heart rate HR is deviated from an upper limit or lower limit of a predetermined reference range. Further, an amplitude value A of the heartbeat signal SH is calculated, and an abnormality determination of the cardiac output is made, for example, in a case when the calculated amplitude value A is deviated from an upper limit or lower limit of a predetermined reference range. Further, the functional abnormality or anatomic abnormality of two atria and two ventricles constituting the heart 26 is evaluated, based on the heartbeat signal SH analyzed by the waveform analysis controlling portion 72. For example, a correlation coefficient C between the heartbeat waveform represented by the heartbeat signal SH and pre-stored plurality of kinds of abnormality evaluation patterns is calculated. The functional abnormality or anatomic abnormality of two atria and two ventricles constituting the heart 26, which is indicated by the abnormality evaluation pattern in which the correlation coefficient C exceeds a predetermined determination value, is determined, and the degree of the abnormality is evaluated.

Then, at S5, the abnormality of the heart rate HR, abnormality of the amplitude value A (cardiac output), or functional abnormality or anatomic abnormality of the two atria and two ventricles constituting the heart 26 is outputted through the display of the display device 76. Thus, it is possible to evaluate not only a drug effect of a circulatory system drug having a chronotropic effect that changes a heart rate but also a drug effect of a circulatory system drug having an inotropic effect that changes a cardiac output. Particularly, the capability of making the evaluation of the drug effect of a circulatory system drug having an inotropic effect that changes a cardiac output is advantageous because such an evaluation cannot be made by ECG (electrocardiogram). Further, under an artificial respiration management, particularly, in a situation where a positive end expiratory pressure (PEEP) is employed to prevent an alveolar collapse and improve a lung oxygenation by applying a pressure higher than an atmospheric pressure at an end-tidal stage, it is considered that pressure of alveoli limits an expansion of volume of the heart 26 that is adjacent to the alveoli and affects a hemodynamics. The abnormality in which the expansion of the heart 26 is limited is evaluated based on the correlation coefficient between the abnormality evaluation pattern reflecting such a situation and the heartbeat waveform represented by the heartbeat signal SH.

As described above, in the heartbeat-signal detecting device 30 of the present embodiment, the frequency components, which are in synchronization with the pulse of the heart 26 of the living body 10 superimposed on the respiration signal SR, are extracted from the respiration signal SR outputted from the gas-flow calculation controlling portion 70, by the waveform analysis controlling portion 72, and the heartbeat signal SH representing the pulse is outputted. Thus, the heartbeat signal SH representing the ejection of the heart 26 of the living body 10 can be easily detected by using the heartbeat signal SH, without using ECG electrodes attached to the living body 10. That is, the heartbeat signal SH can be easily obtained even in a case of an infant where it is difficult to keep the ECG electrodes attached to his or her skin for a long time for the purpose of electrocardiograph measurement because the skin is delicate. Further, the heartbeat signal SH reflecting a cardiac output, i.e., an actual volumetric change of the heart 26 can be obtained, and therefore, as compared with a conventional device using an electrocardiographic induction waveform, it is possible to confirm the presence or absence of a pulse of the heart 26 with higher reliability, perform quickly a medical treatment at an emergency lifesaving site, and evaluate clinically a circulatory system drug that changes not only a heart rate HR but also a cardiac output.

In the heartbeat-signal detecting device 30 of the present embodiment, the gas-flow sensor 36 is configured to detect a flow speed of the gas passing through the tubular case 46, based on a change of an electric resistance of the heater element 52 that is heated by electricity supplied thereto, wherein the electric resistance is changed depending on the flow speed. The heater element 52 is constituted by an electric resistance element whose electric resistance is changed depending on a temperature, wherein the electric resistance is constituted by, for example, a platinum resistance element or a gold resistance element. The heater element 52 is provided on an inner surface of the circuit substrate film 50 which is disposed along an inner wall surface of the tubular case 46 and which is spaced apart from the inner wall surface by a predetermined space S. Owing to this construction, even where the tubular case 46 is made of a flexible material, since the heater element 52 is provided on the inner wall surface of the tubular case 46 so as to extend along a shape of the inner wall surface and to be spaced apart from the inner wall surface by the predetermined space S, the flow rate can be detected in an area having a certain distance, rather than being detected at a point, so that the flow rate can be measured even if the tube is curvy. Further, owing to the provision of the space S for insulating the heat transmission between the heater element 52 and the tubular case 46, the responsiveness with respect to the heat is dependent on a heat capacity of the heater element 52 itself, thereby consequently making it possible to realize a high-speed response.

In the heartbeat-signal detecting device 30 of the present embodiment, the gas-flow sensor 36 has the bridge circuits (electric bridges) 56a, 56b. Each of the bridge circuits 56a, 56b includes four resistance elements, one of which is constituted by a corresponding one of the heater elements 52a, 52b. The gas flow rate is detected in accordance with a pre-stored relationship of FIG. 7 between the flow rate FR and the square value $Vout^2$ of the output voltage Vout of the gas-flow-speed measuring circuit 38, which reflects the output voltages Vout1, Vout2 of the respective bridge circuits 56a, 56b, and based on the actual output voltage Vout of the gas-flow-speed measuring circuit 38. Thus, the measurement of the flow rate FR can be made advantageously with high accuracy.

In the heartbeat-signal detecting device 30 of the present embodiment, the waveform analysis controlling portion 72 is configured to remove, from the respiration signal SR outputted from the gas-flow calculation controlling portion 70, the frequency components which are in synchronization with the pulse of the heart 26 of the living body 10 superimposed on the respiration signal SR, and to output the ventilation component signal SR0 representing the lung capacity component originating from the thorax 18 and the thoracic diaphragm 20 of the living body 10. This arrangement enables the ventilation component signal SR0 and the heartbeat signal SH to be simultaneously obtained, so that medical services can be performed advantageously in a short time at an emergency medical site with limitation in time.

In the heartbeat-signal detecting device 30 of the present embodiment, the heartbeat-signal evaluation controlling portion 74 is provided to evaluate a functional abnormality or an anatomic abnormality of two atria and two ventricles constituting the heart 26, based on the heartbeat signal SH analyzed by the waveform analysis controlling portion 72. Thus, not only the heartbeat signal SH can be obtained but also the functional abnormality or anatomic abnormality of the two atria and two ventricles constituting the heart 26 can be known based on the heartbeat signal SH.

Next, other embodiments of the present invention will be described hereinafter. In the following description, the same reference sings as used in the preceding embodiment will be used to identify elements common to the embodiments, and the common elements will not be described.

Embodiment 2

Figure 13:
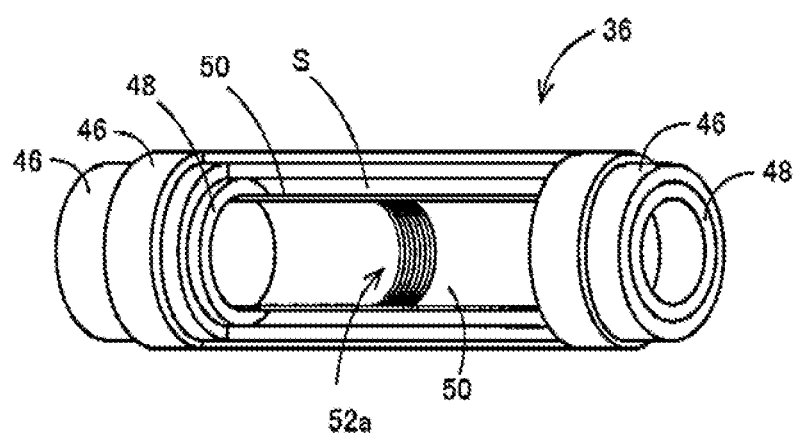
FIG. 13 is a perspective view showing a construction of a gas-flow sensor according to another embodiment of the invention, and corresponding to the view of FIG. 4.
Figure 14:
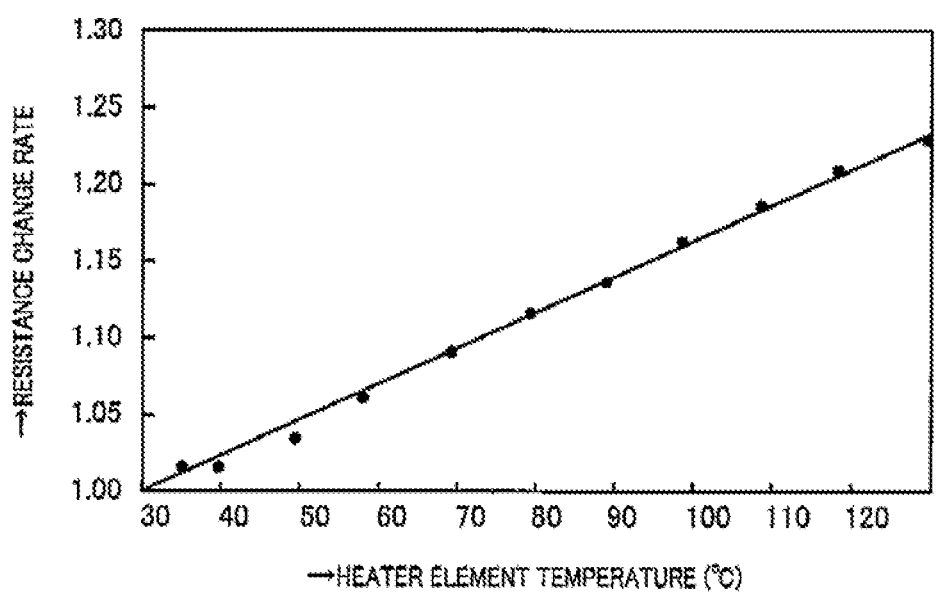
FIG. 14 is a view showing a characteristic of a rate of change of resistance of a heat element shown in FIG. 13, in relation with temperature.
Figure 15:
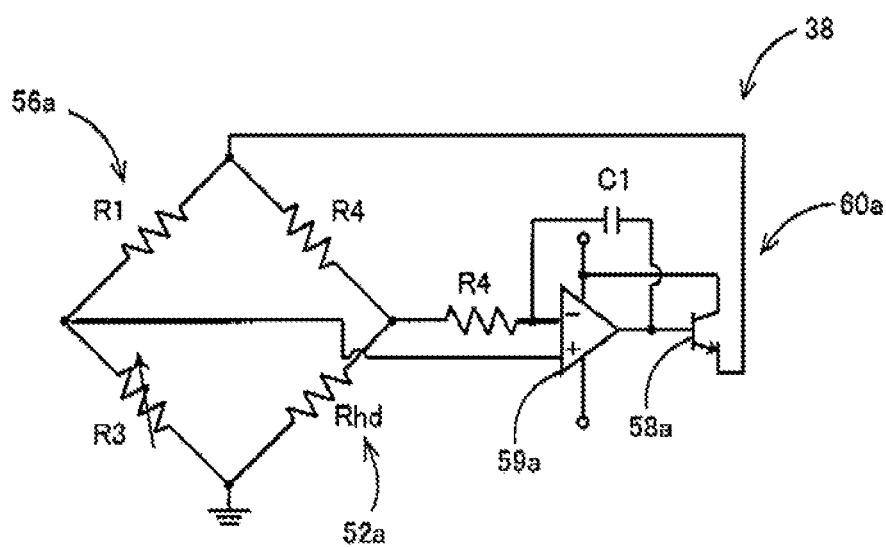
FIG. 15 is a circuit diagram explaining a construction of a gas-flow rate electric circuit used for the gas-flow sensor of the embodiment shown in FIG. 13, and corresponding to the circuit diagram of FIG. 6.

In the gas-flow sensor 36 in the above-described embodiment, the pair of heater elements 52a, 52b are provided. However, a single heater element may be provided, as shown in FIG. 13. In this case, although the direction of flow of air is not made clear, the gas-flow rate can be measured. FIG. 13 is a perspective view showing the gas-flow sensor 36 having the single heater element 52a, and corresponding to the view of FIG. 4. FIG. 14 is a view showing a resistance change characteristic TCR indicating a rate of change of resistance value of the heater element 52a in relation with temperature, wherein the indicated rate of change is a value relative to 100, which is a value when the temperature is 30° C. FIG. 15 is a view showing a circuit indicating a construction of a gas-flow rate measuring circuit for operating the gas-flow sensor 36 with the single heater element 52a, and corresponding to the view of FIG. 6. As shown in FIG. 15, the gas-flow-speed measuring circuit 38 includes the first bridge circuit 56a and the first measuring circuit 60a, wherein the first bridge circuit 56a is constituted by four resistors, i.e., the resistors R1, R2, R3 and the heater element 52a (resistance value Rhd), and a first bridge power-supply voltage Vs1 is applied to the first bridge circuit 56a, and wherein the first measuring circuit 60a includes the first feedback amplifier 59a configured to amplify an output voltage Vout1 of the first bridge circuit 56a and the first transistor 58a configured to supply an electric current corresponding to the output voltage Vout1, to the first bridge circuit 56a. The above-descried output voltage Vout1 represents the gas flow speed. The above-described resistor R3 is a variable resistor configured to adjust an equilibrium state of the first bridge circuit 56a.

Embodiment 31

Figure 16:
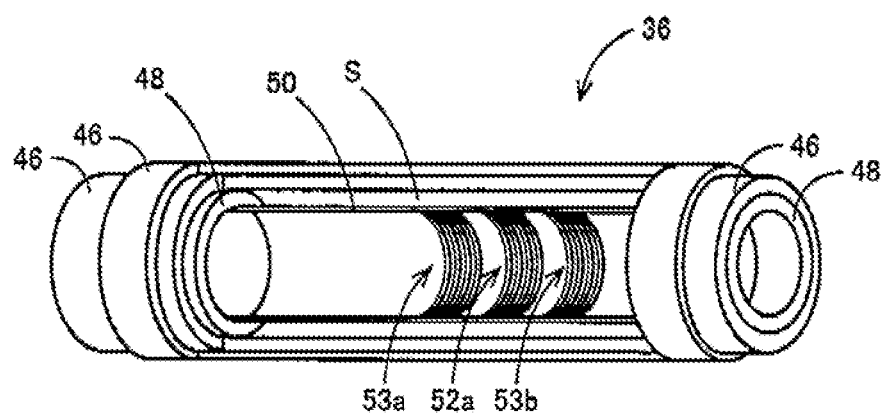
FIG. 16 is a perspective view corresponding to the view of FIG. 4 and showing, by way of example, a gas-flow sensor according to another embodiment of the invention in which a pair of detection resistor elements are provided on respective opposite sides of a heater element, wherein the detection resistor elements are configured to measure the flow rate, based on change of the resistance value.

FIG. 16 shows an example in which a pair of detection resistor elements 53a, 53b are provided on respective opposite sides of the heater element 52a, wherein the detection resistor elements 53a, 53b are configured to measure the flow rate, based on change of the resistance value. In the gas-flow sensor 36 of the present embodiment, the detection resistor elements 53a, 53b are separated from the heater element 52a, so that an accuracy of measurement of the flow rate can be made higher than in the gas-flow sensor 36 having the single heater element 52a. In the present embodiment, for example, the measuring circuit shown in FIG. 6 is connected to the detection resistor elements 53a, 53b, and a heating control circuit is connected to the heater element 52a, for heating the heater element 52a to a constant temperature.

Embodiment 4

Figure 17:
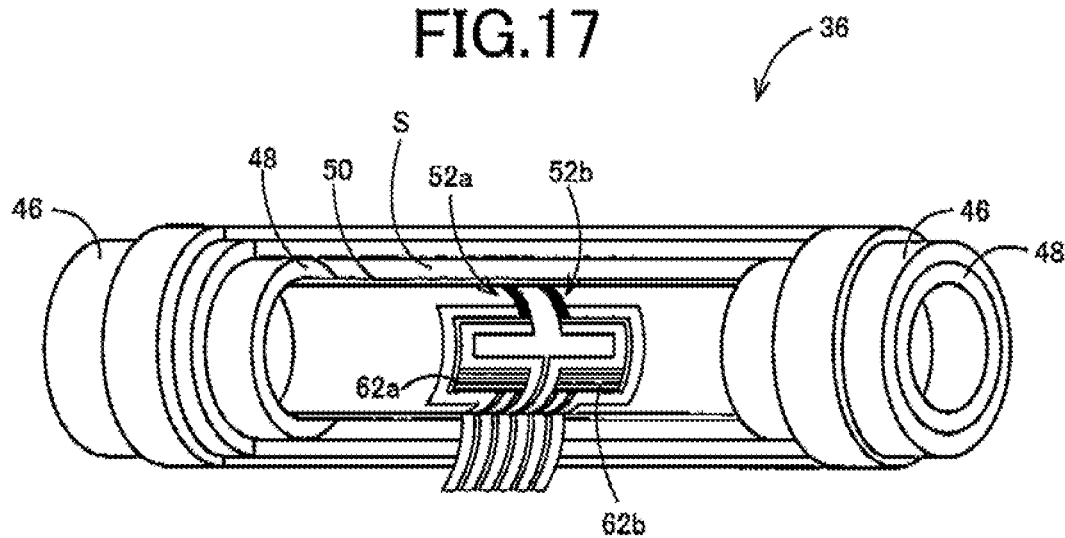
FIG. 17 is a perspective view corresponding to the view of FIG. 4 and showing, by way of example, a gas-flow sensor according to another embodiment of the invention in which a pair of heater elements and a pair of temperature compensation elements are provided.
Figure 18:
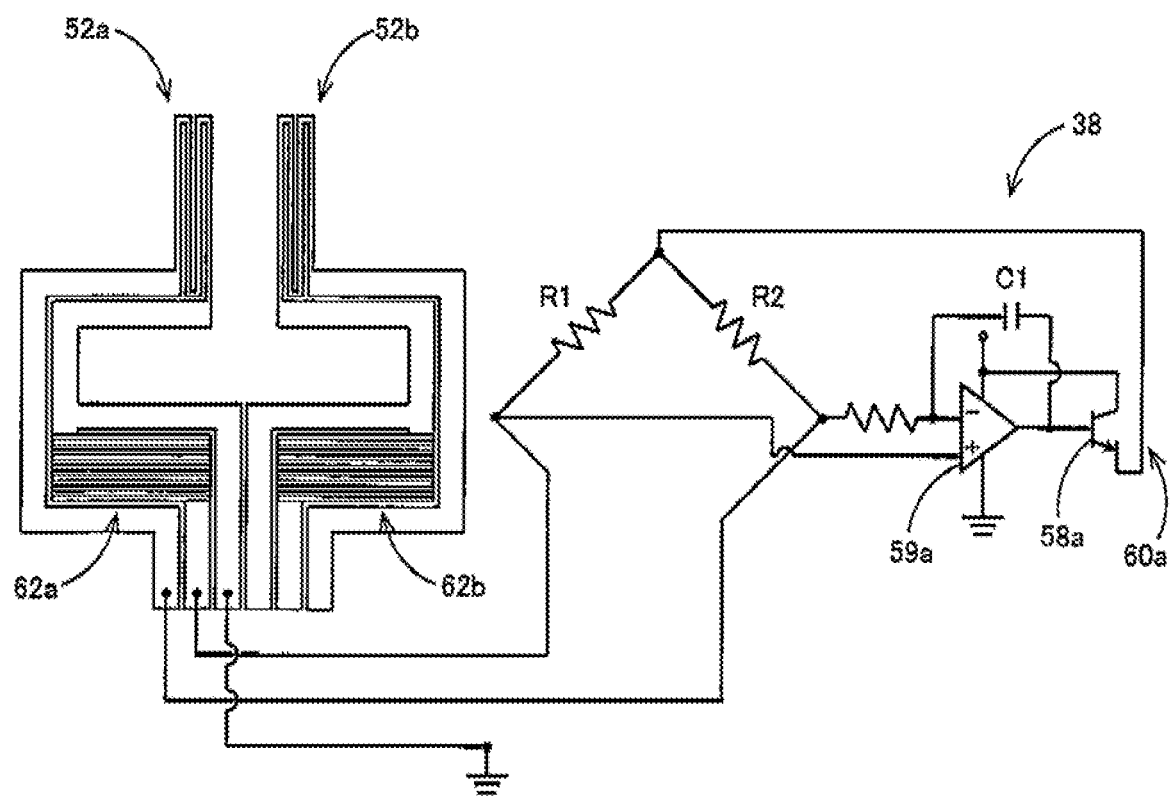
FIG. 18 is a circuit diagram showing a first measuring circuit as a part of a measuring circuit used for the gas-flow sensor shown in FIG. 17.
Figure 19:
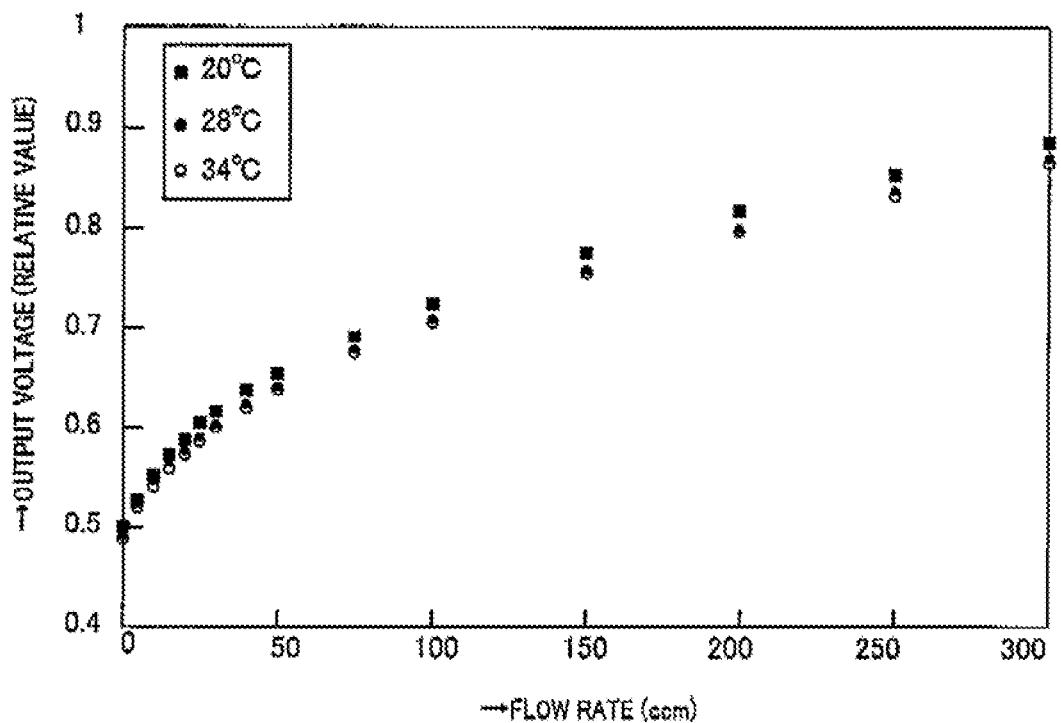
FIG. 19 is a view showing an output voltage characteristic of the gas-flow sensor shown in FIGS. 17 and 18 and using the temperature compensation elements, in relation with the flow rate, wherein the output voltage characteristic was obtained at each of various air temperatures.
Figure 20:
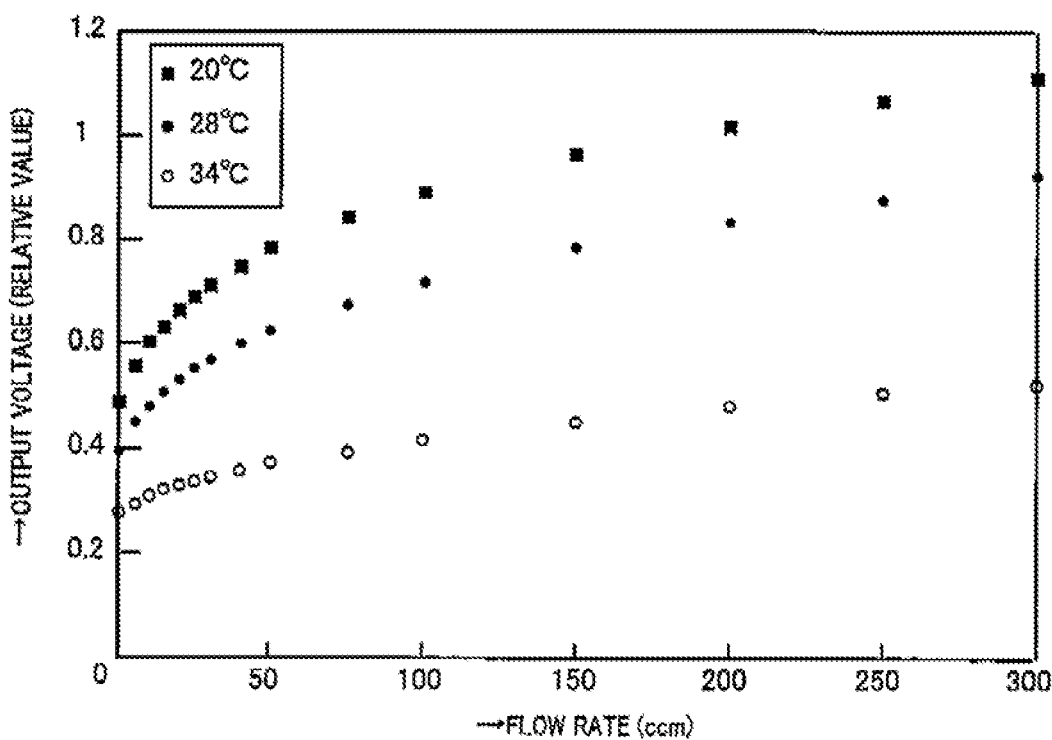
FIG. 20 is a view showing an output voltage characteristic in relation with the flow rate in a case where the temperature compensation elements were not used, wherein the output voltage characteristic was obtained at each of various air temperatures.

The above-described gas-flow sensor 36 having the pair of heater elements 52a, 52b, which is shown in FIG. 4, may be provided with a pair of temperature compensation elements 62a, 62b, as shown in FIG. 17. FIG. 18 shows the first measuring circuit 60a that is a part of the measuring circuit 38. Each of the temperature compensation elements 62a, 62b has an electric resistance value that is at least as large as ten times that of each of the heater element 52a, 52b, so as to restrain the self-heating. The temperature compensation elements 62a, 62b are provided together with the heater elements 52a, 52b, by sputtering, on the same substrate under the same condition, so that the temperature compensation elements 62a, 62b have the same resistance-temperature characteristic as the heater elements 52a, 52b. FIG. 19 shows an output voltage characteristic in relation with the flow rate in a case where the temperature compensation elements 62a, 62b were used, wherein the output voltage characteristic was obtained at each of various gas temperatures. FIG. 20 shows an output voltage characteristic in relation with the flow rate in a case where the temperature compensation elements 62a, 62b were not used, wherein the output voltage characteristic was obtained at each of various gas temperatures. The output voltage was reduced at 34° C. as compared with that at 20° C., by 50% in the case shown in FIG. 20, and by 2% or less in the case shown in FIG. 19.

Embodiment 5

Figure 21:
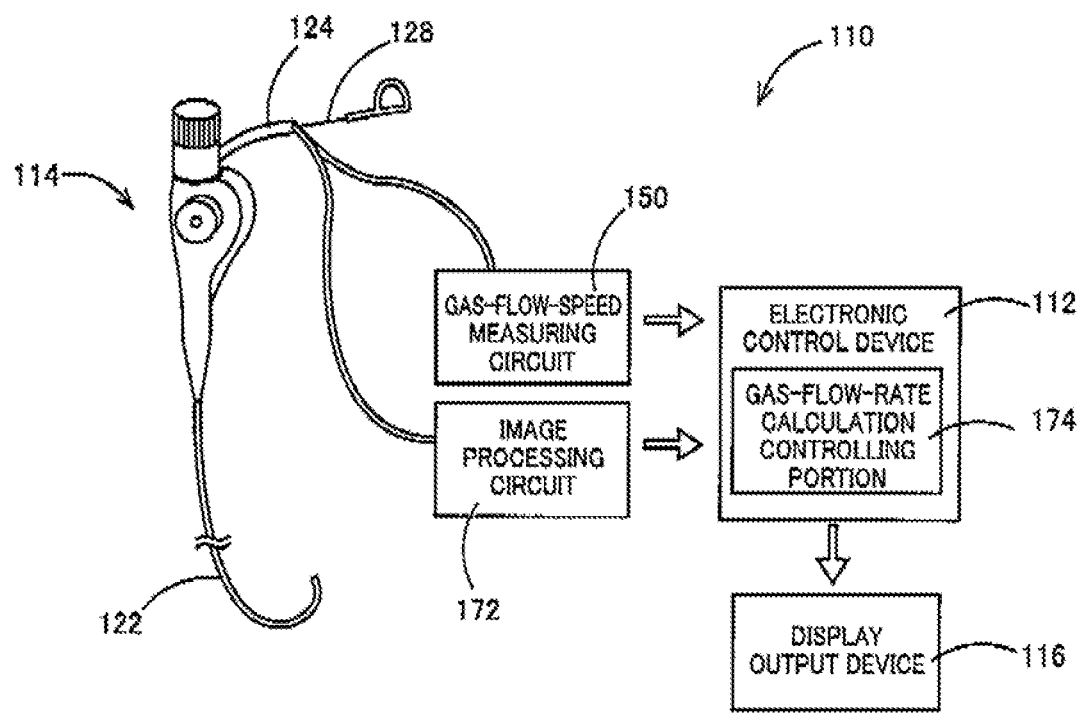
FIG. 21 is a view explaining constructions of an airway gas-flow rate measuring device including another embodiment of the invention, and also a main portion of a control function of an electronic control device included in the airway gas-flow rate measuring device.

FIG. 21 is a view explaining constructions of an airway gas-flow rate measuring device 110 and a gas-flow sensor 126 provided in the measuring device 110, and also functions of an electronic control device 112 provided in the measuring device 110. The airway gas-flow rate measuring device 110 includes a bronchoscope 114 and a display output device 116 in addition to the electronic control device 112 and gas-flow sensor 126. The gas-flow sensor 126 may be any of two heater-elements type in Embodiment 1 shown in FIG. 4, one heater-element type in Embodiment 2 shown in FIG. 13, a type in Embodiment 3 shown in FIG. 16, and two heater-elements type with a pair of temperature compensation elements in Embodiment 4 shown in FIG. 17. However, in this Embodiment 5, the gas-flow sensor 126 is two heater-elements type, by way of example.

Figure 22:
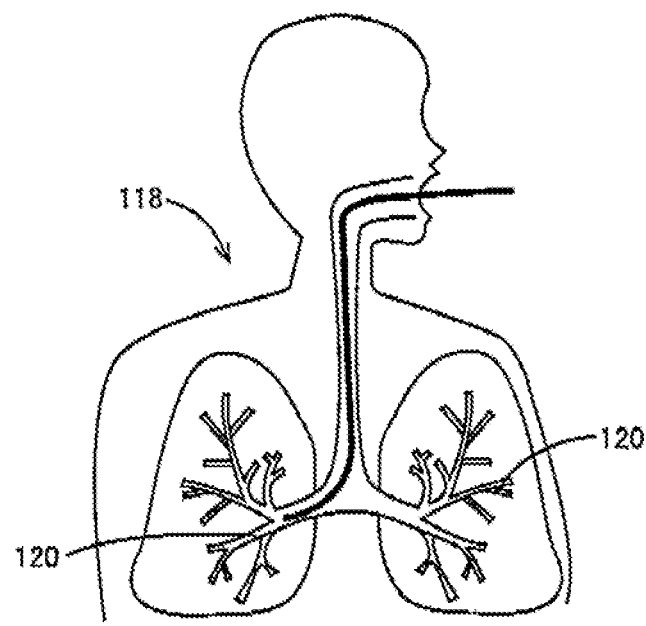
FIG. 22 is a schematic view showing lungs and airways of a living body.
Figure 23:
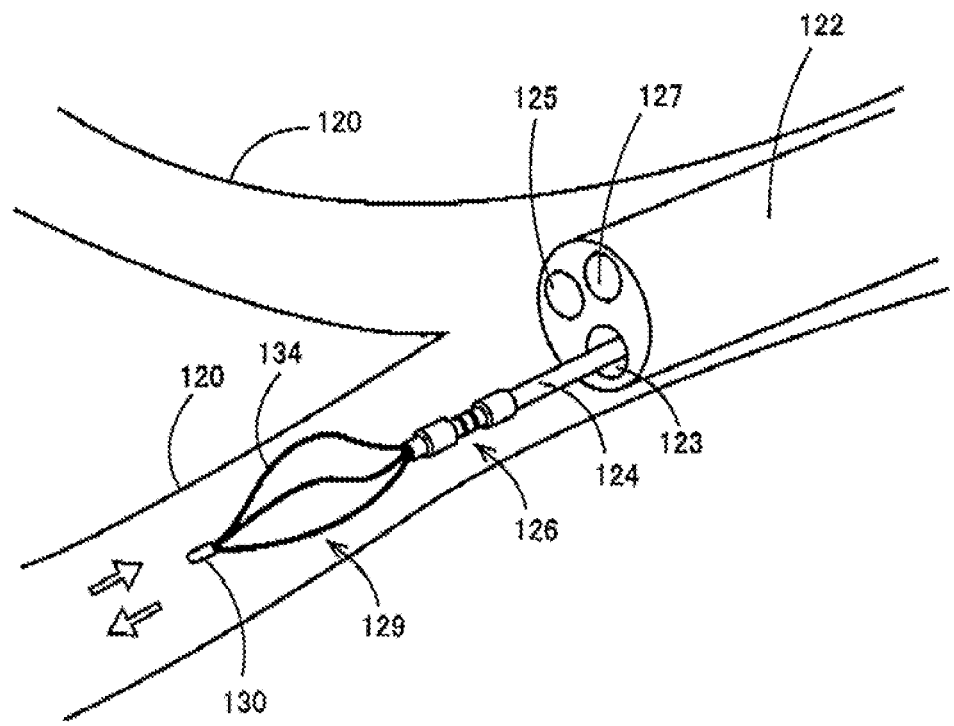
FIG. 23 is a schematic view showing a catheter protruding from a distal end portion of a bronchoscope that is inserted in the airway shown in FIG. 22 or from a distal end of a longitudinally-extending through-hole of the bronchoscope, and also a gas-flow sensor and a diameter expansion basket provided in a distal end portion of the catheter.

The bronchoscope 114 includes a flexible sheath 122 that is inserted into an airway 120 of a living body 118 as shown in shown in FIG. 22. The flow rate of the gas passing through the airway is measured by using a gas-flow measuring catheter 124, the above-described gas-flow sensor 126, an operating wire 128 and a diameter expansion basket 129. As shown in FIG. 23, the gas-flow measuring catheter 124 is provided to pass through the flexible sheath 122 and is operable to protrude from a distal end of the flexible sheath 122. The gas-flow sensor 126 is provided in a distal end portion of the gas-flow measuring catheter 124. The operating wire 128 is provided to pass through the gas-flow measuring catheter 124 and is operable to protrude from a distal end of the gas-flow measuring catheter 124. The diameter expansion basket 129 is provided in a distal end portion of the operating wire 128. As shown in FIG. 23, in a distal end face of the flexible sheath 122, there are provided a light source 125 and a CCD camera 127 in addition to an opening of a longitudinally-extending through-hole 123 through which the gas-flow measuring catheter 124 is caused to pass.

Figure 24:
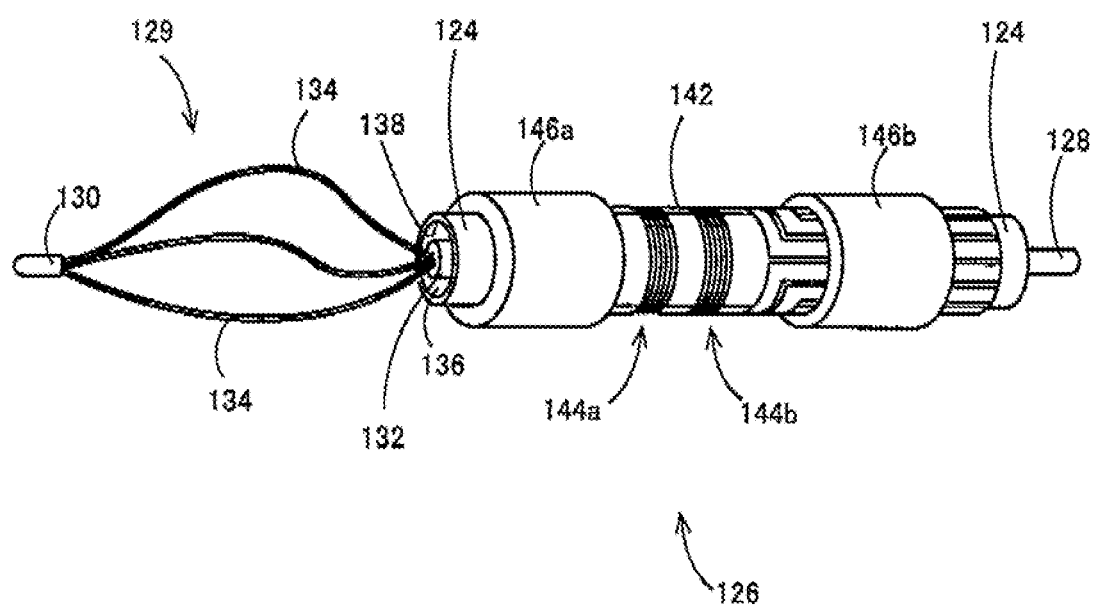
FIG. 24 is a perspective view showing, in enlargement, the gas-flow sensor and the diameter expansion basket provided in the distal end portion of the catheter shown in FIG. 23.

FIG. 24 is a perspective view showing, in enlargement, the gas-flow sensor 126 provided in the distal end portion of the gas-flow measuring catheter 124 that protrudes from the flexible sheath 122, and the diameter expansion basket 129 protruding from the distal end of the gas-flow measuring catheter 124. In the present embodiment, in the distal end portion of the gas-flow measuring catheter 124, the diameter expansion basket 129 is provided on a distal end side of the gas-flow sensor 126. This diameter expansion basket 129 includes a plurality of elastic wires 134 that are bundled at their distal and rear end portions by a distal end tip 130 and a rear end tip 132, and is fixed to the distal end portion of the gas-flow measuring catheter 124. The diameter expansion basket 129 is restrained by an inner wall of a longitudinally-extending through-hole 136 of the gas-flow measuring catheter 124, when being in the through-hole 136, and an diameter of the diameter expansion basket 129 expands owing to elastic forces of the elastic wires 134, when protruding out from an opening 138 of the through-hole 136.

Figure 25A:
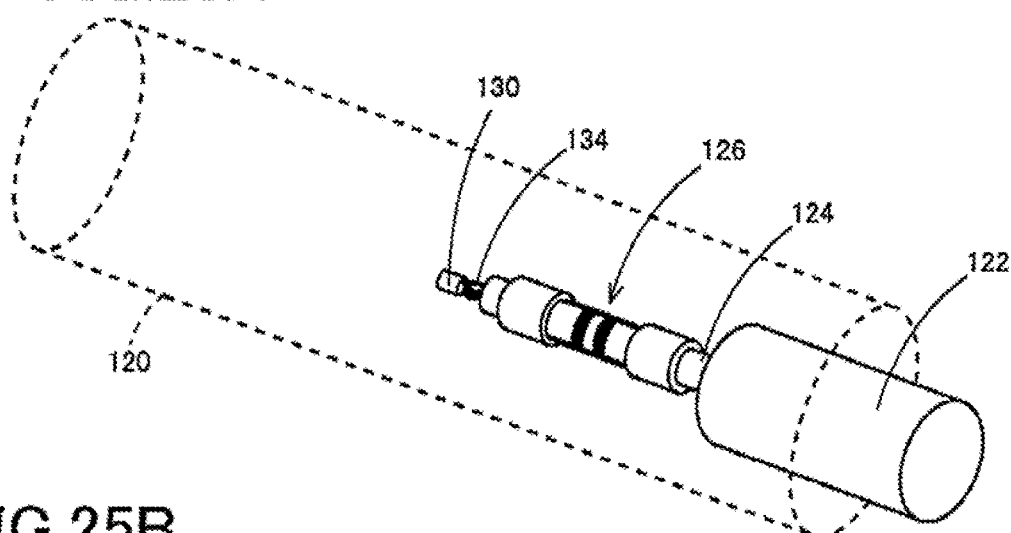
FIG. 25 is a set of perspective views showing an operation for expanding the diameter expansion basket from the gas-flow measuring catheter having the distal end portion in which the gas-flow sensor of FIG. 24 is provided, wherein the view (a) shows a state before the diameter expansion basket is caused to protrude from the gas-flow measuring catheter, the view (b) shows a state in which the diameter expansion basket is being caused to protrude from the gas-flow measuring catheter and the view (c) shows a state after the diameter expansion basket has been caused to protrude from the gas-flow measuring catheter.
Figure 25B:
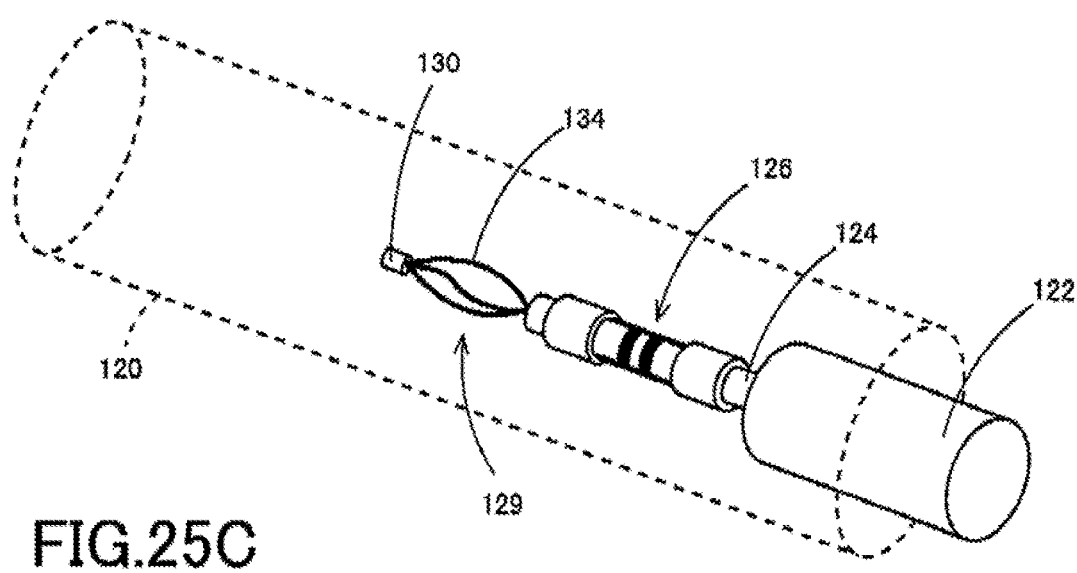
Figure 25C:
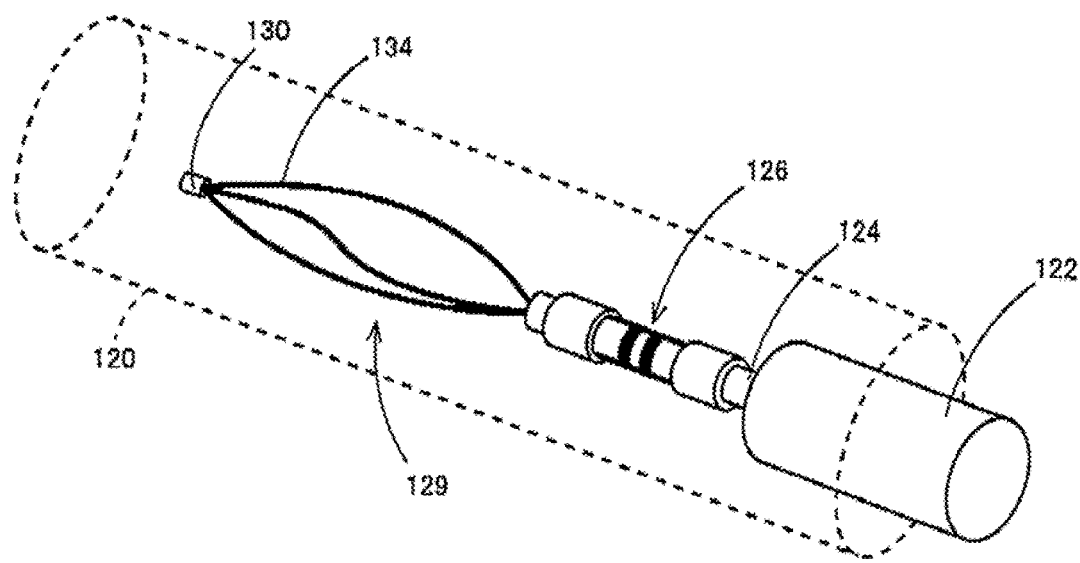

As shown in FIG. 25(a), the gas-flow measuring catheter 124 is caused to protrude from the distal end face of the flexible sheath 122, and the gas-flow sensor 126 is exposed in the airway 120. As shown in FIG. 25(b), the operating wire 128 is caused to protrude from the distal end face of the gas-flow measuring catheter 124. As shown in FIG. 25(c), in a measuring state in which the diameter of the diameter expansion basket 129 is increased in the airway 120, the gas-flow sensor 126, which is provided in the distal end portion of the gas-flow measuring catheter 124 and which is contiguous to the diameter expansion basket 129 on the side of the flexible sheath 122, is positioned in a central portion of the airway 120.

Figure 26:
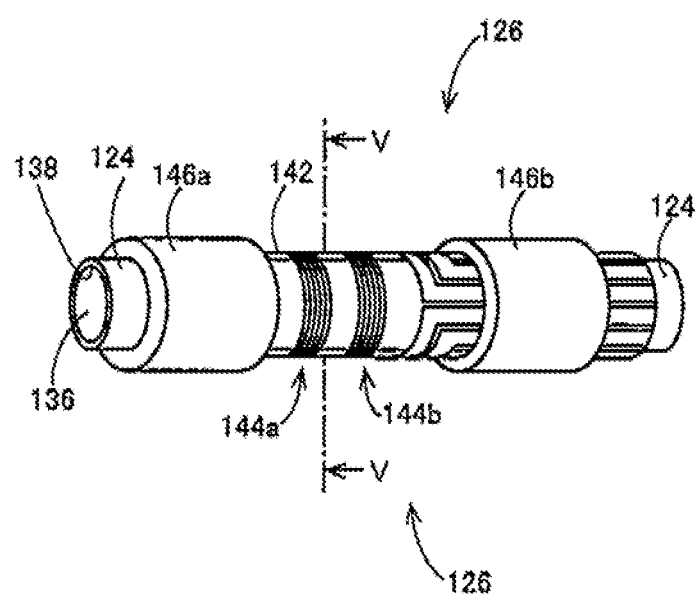
FIG. 26 is a perspective view explaining a mechanical construction of the gas-flow sensor shown in FIG. 24.
Figure 27:
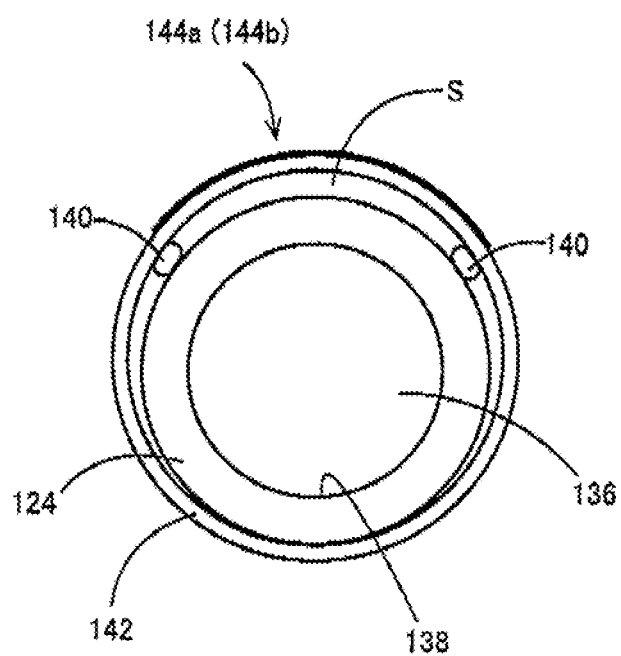
FIG. 27 is a cross sectional view of the gas-flow sensor of FIG. 26, which is taken in line V-V.

FIG. 26 is a perspective view explaining a construction of the gas-flow sensor 126. FIG. 27 is a transverse cross-sectional view of the gas-flow sensor 126. As shown in FIGS. 26 and 27, the gas-flow sensor 126 includes a circuit substrate film 142, a pair of heater elements 144a, 144b and a pair of annular fixing members 146a, 146b. The circuit substrate film 142 is wound on a distal end portion of the gas-flow measuring catheter 124, which functions as a first sensor substrate, via a pair of spacers 140, and is made of parylene resin, epoxy resin, polyimide resin or other electrically insulated material having flexibility. The heater elements 144a, 144b are deposited to be provided on an outer circumferential surface of the circuit substrate film 142 by photoetching and made of platinum film, gold film or other metal thin film whose electric resistance is changed depending on temperature, such that the heater elements 144a, 144b are spaced apart from each other by a predetermined space in a direction of an axis of the gas-flow measuring catheter 124. The pair of annular fixing members 146a, 146b are provided to fix respective end portions of the circuit substrate film 142, which are opposite to each other in the direction of the axis, to the distal end portion of the gas-flow measuring catheter 124. The gas-flow sensor 126 is configured to detect the flow rate of the gas passing through the airway 120, based on a change of an electric resistance of the heater elements 144a, 144b that are heated by electricity supplied thereto, wherein the electric resistance is changed depending on the flow rate of the gas passing through the airway 120. The annular fixing members 146a, 146b are resin components for fixing the above-described opposite end portions of the circuit substrate film 142 to the distal end portion of the gas-flow measuring catheter 124, by bonding or crimping. The circuit substrate film 142 is bonded to the distal end portion of the gas-flow measuring catheter 124, for example, by adhesive. Where the annular fixing members 146a, 146b are made of heat-shrinkable resin, the circuit substrate film 142 is crimped to the distal end portion of the gas-flow measuring catheter 124 by heat shrinkage of the annular fixing members 146a, 146b.

Figure 28:
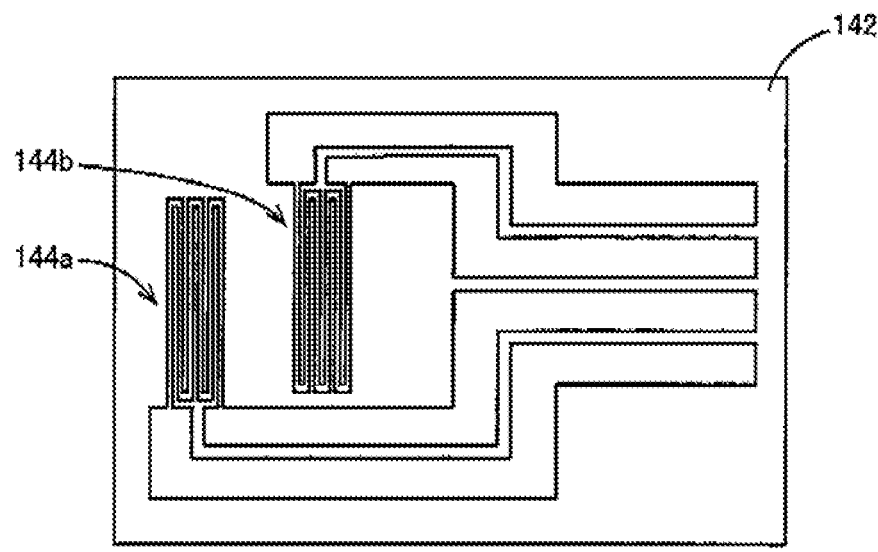
FIG. 28 is a development view showing a flexible circuit substrate film shown in FIGS. 24 and 26, on which heater elements are provided.
Figure 29:
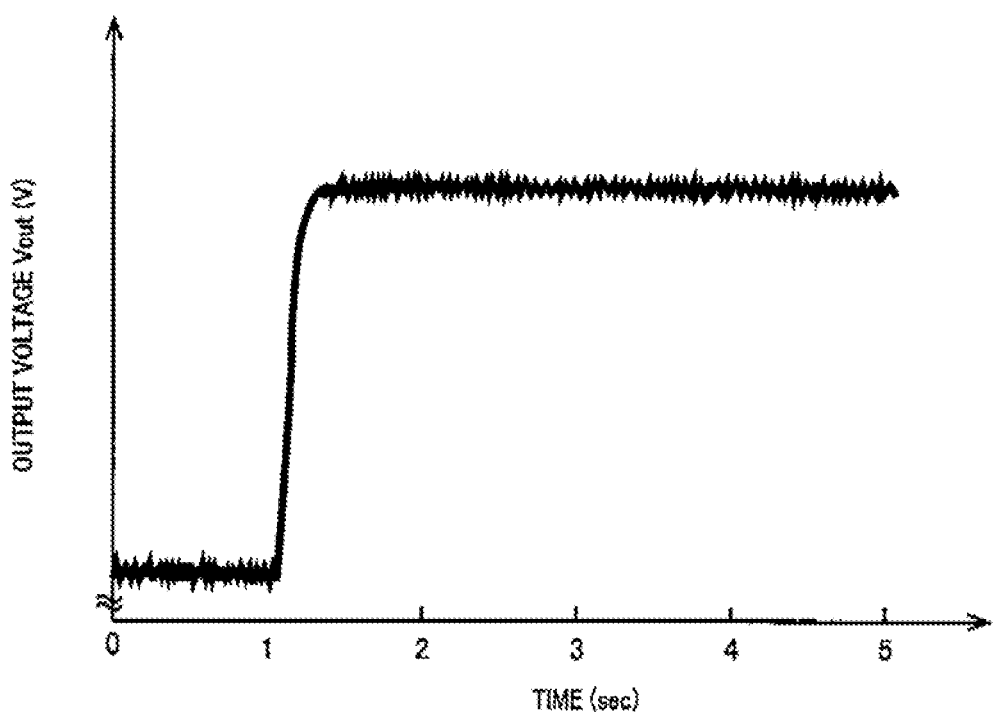
FIG. 29 is a view showing a responsiveness of the gas-flow sensor shown in FIGS. 25 and 26.

As shown in FIG. 27, owing to the pair of spacers 140 interposed between the circuit substrate film 142 and an outer circumferential surface of the distal end portion of the gas-flow measuring catheter 124, a space S is defined between the outer circumferential surface of the distal end portion of the gas-flow measuring catheter 124 and at least portions of the circuit substrate film 142 in which the pair of heater elements 144a, 144b are provided, whereby the heater elements 144a, 144b are thermally insulated from each other. FIG. 28 is a development view showing the circuit substrate film 142 that is wound on the distal end portion of the gas-flow measuring catheter 124 via the pair of spacers 140. FIG. 29 shows change of the resistance value of the heater elements 144a, 144b, i.e., change of the output voltage Vout of a gas-flow-speed measuring circuit 150 that is described below, which were obtained when the gas flow was started experimentally. In FIG. 29, the output voltage Vout indicates a high responsiveness owing to a low heat capacity of the heater elements 144a, 144b and the thermal insulation effect of the above-described space S.

Figure 30:
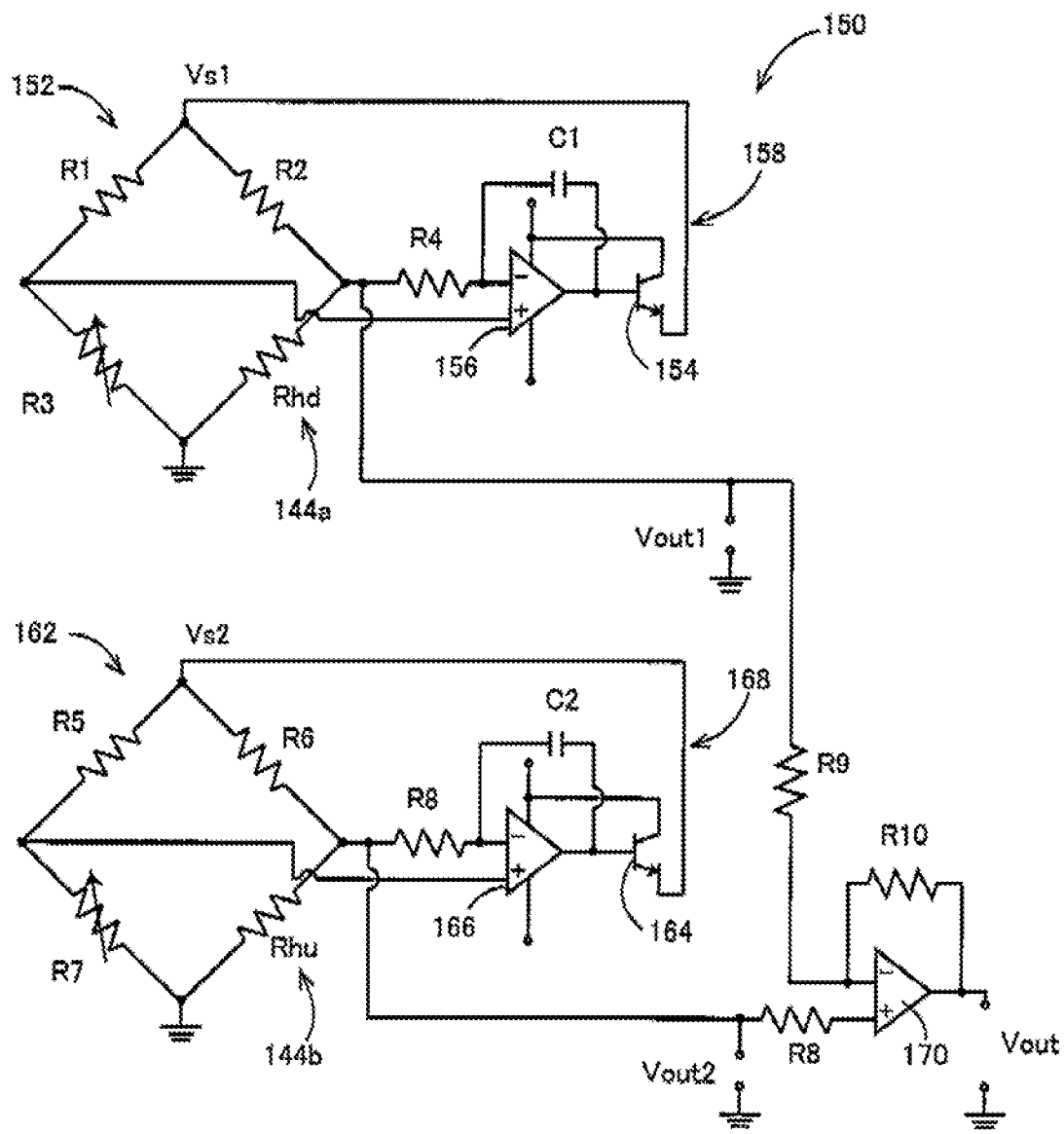
FIG. 30 is a circuit diagram explaining a construction of a gas-flow-speed measuring circuit including the heater elements of the gas-flow sensor of FIG. 24.

FIG. 30 shows a construction of a constant-temperature type measuring circuit as an example of the gas-flow-speed measuring circuit 150. As shown in FIG. 30, the gas-flow-speed measuring circuit 150 includes a first bridge circuit 152 and a first measuring circuit 158, wherein the first bridge circuit 152 is constituted by four resistors, i.e., resistors R1, R2, R3 and the heater element 144a (resistance value Rhd), and a first bridge power-supply voltage Vs1 is applied to the first bridge circuit 152, and wherein the first measuring circuit 158 includes a first feedback amplifier 156 configured to amplify an output voltage Vout1 of the first bridge circuit 152 and a first transistor 154 configured to supply an electric current corresponding to the output voltage Vout1, to the first bridge circuit 152. The gas-flow-speed measuring circuit 150 further includes a second bridge circuit 162 and a second measuring circuit 168, wherein the second bridge circuit 162 is constituted by four resistors, i.e., resistors R5, R6, R7 and the heater element 144b (resistance value Rhu), and a second bridge power-supply voltage Vs2 is applied to the second bridge circuit 162, and wherein the second measuring circuit 168 includes a second feedback amplifier 166 configured to amplify an output voltage Vout2 of the second bridge circuit 162 and a second transistor 164 configured to supply an electric current corresponding to the output voltage Vout2, to the second bridge circuit 162. The gas-flow-speed measuring circuit 150 still further includes a differential amplifier 170 configured to amplify a difference voltage between the output voltage Vout1 of the first bridge circuit 152 and the output voltage Vout2 of the second bridge circuit 162, and then to output an output voltage Vout. The above-described resistor R3 is a variable resistor configured to adjust an equilibrium state of the first bridge circuit 152. The above-described resistor R7 is a variable resistor configured to adjust an equilibrium state of the second bridge circuit 162.

In the gas-flow-speed measuring circuit 150 constructed as described above, when the gas flow speed is suddenly increased from the equilibrium state in the first bridge circuit 152, the temperature of the first heater element 144a is reduced whereby the resistance value Rhd is reduced. In this instance, for restoring the equilibrium state of the first bridge circuit 152, the first bridge power-supply voltage Vs1 is increased by the first feedback amplifier 156 whereby the temperature of the first heater element 144a is increased and is held in a constant temperature. Similarly, when the gas flow speed is suddenly increased from the equilibrium state in the second bridge circuit 162, the temperature of the second heater element 144b is reduced whereby the resistance value Rhu is reduced. In this instance, for restoring the equilibrium state of the second bridge circuit 162, the second bridge power-supply voltage Vs2 is increased by the feedback amplifier 166 whereby the temperature of the first heater element 144b is increased and is held in a constant temperature. In the gas-flow-speed measuring circuit 150, the output voltage Vout, which is outputted from the differential amplifier 170 and which represents the difference voltage between the output voltage Vout1 of the first bridge circuit 152 and the output voltage Vout2 of the second bridge circuit 162, constitutes a signal reflecting a difference between resistance changes in the respective heater elements 144a, 144b, namely, forms a waveform representing a forward direction or reverse direction as the direction of the gas flow through the airway 120. That is, the output voltage Vout constitutes a signal represents the direction of the gas flow, by a waveform consisting of one peak and one trough in one respiratory cycle.

The flow rate FR (cc/min) is calculated in accordance with, for example, a pre-obtained calibration curve which is substantially the same as that shown in FIG. 7, i.e., a relationship between the flow speed FS (cm/sec) and a square value of an output voltage, and based on one of the output voltage Vout1 and output voltage Vout2 outputted from the respective first and second bridge circuits 152, 162 containing the respective heater elements 144a, 144b, wherein the one of the output voltage Vout1 and output voltage Vout2 is outputted from one of the bridge circuits whose heater element is located on an upstream side. The above-described one of the output voltage Vout1 and output voltage Vout2 is selected depending on whether the output voltage Vout of the gas-flow-speed measuring circuit 150 is positive or negative. The flow rate FR (cc/min) of the gas flowing through the gas-flow sensor 126 is obtained, by multiplying the output voltage Vout1 or output voltage Vout2 outputted from the gas-flow-speed measuring circuit 150 and representing the flow speed FS (cm/sec), with a pre-obtained flow cross-sectional area C (constant) of the gas-flow sensor 126. It is noted that the flow speed FS (cm/sec) may be used for the abscissa in the relationship shown in FIG. 7, in place of the gas-flow-rate.

In the first measuring circuit 158, the change of the resistance value Rhd of the heater element 144a can be obtained from any one of the output voltage Vout1 of the first bridge circuit 152, the output voltage (V) of the first feedback amplifier 156, an output current of the first feedback amplifier 156 and an output current of the first voltage regulator 154, because any of these values reflects the change of the resistance value Rhd of the heater element 144a. The same description is applied also in the second measuring circuit 168. Therefore, the output signal of each of the first measuring circuit 158 and second measuring circuit 168 may be a signal presenting the corresponding gas flow speed.

Figure 31:
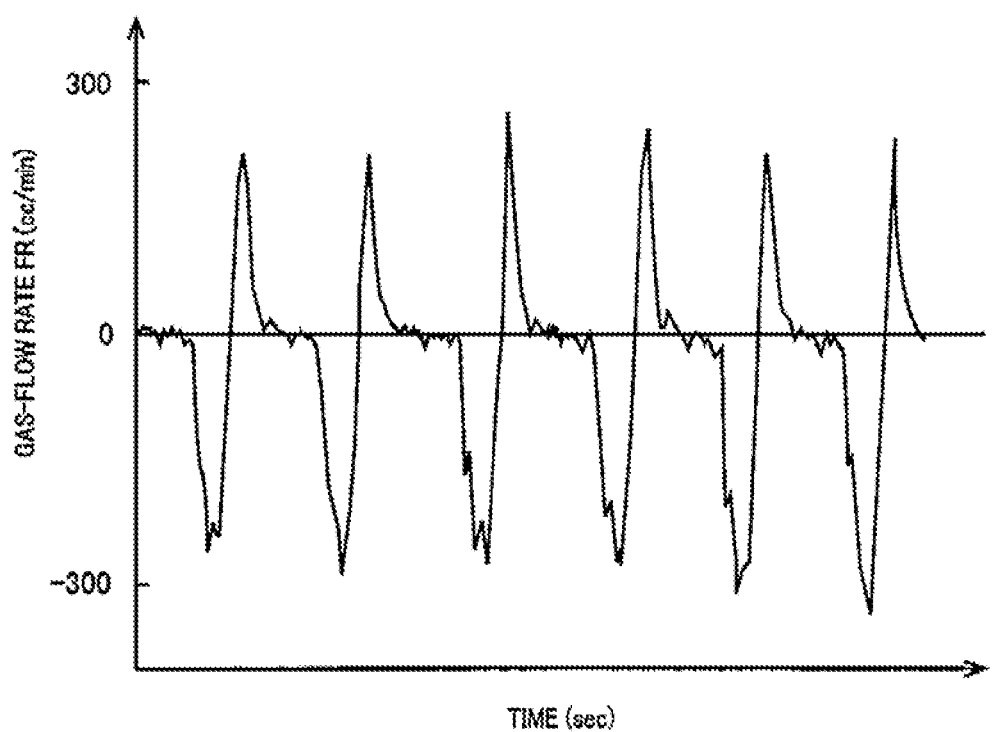
FIG. 31 is a view showing a gas-flow rate in an airway, which was obtained based on an output signal of the gas-flow-speed measuring circuit of FIG. 30.

FIG. 31 shows, by way of example, an experiment in which the respiration of a rat was obtained as a flow rate of a gas passing through the gas-flow sensor 126, by using the gas-flow sensor 126 and the gas-flow-speed measuring circuit 150.

Referring back to FIG. 21, an image processing circuit 172 includes an image taking element configured to convert an image taken through the CCD camera 127 into an electronic signal. The image processing circuit 172 outputs an image showing an inside of the airway 120, i.e., the image converted by the image taking element into the electronic signal, to the electronic control device 112. The electronic control device 112 is constituted by a so-called microcomputer of type in which programs pre-stored in ROM or RAM are to be executed by CPU. The electronic control device 112 includes a gas-flow-rate calculation controlling portion 174 as means for performing control functions, and causes the display output device 116 to display, for example, the flow speed FS or flow rate FR of the gas flowing through the airway 120, which is a result of the signal processing.

The gas-flow-rate calculation controlling portion 174 calculates an inside diameter of a portion of the airway 120 in which the gas-flow sensor 126 is positioned, based on the image which is inputted from the image processing circuit 172 and which shows the inside of the airway 120. In the gas-flow-rate calculation controlling portion 174, there is pre-stored relationships, shown in FIG. 7 by way of example, for respective various inside diameters of the airway 120, wherein each of the relationships is between the flow rate FR(cc/min) of the gas passing through the gas-flow sensor 126 and a square value of a parameter reflecting the output voltages of the respective first and second bridge circuits 152, 162 (e.g., a square value Vout2 of the output voltage Vout of the measuring circuit 150). The gas-flow-rate calculation controlling portion 174 selects one of the pre-stored relationships that corresponds to the actual inside diameter of the airway 120 whose image is taken from the distal end of the flexible sheath 122, and calculates the flow rate FR of the gas passing through the airway 120, in accordance with the selected relationship, and based on the square value $Vout^2$ of the output voltage Vout of the gas-flow-speed measuring circuit 150, which is supplied as the output signal from the gas-flow sensor 126. Then, the gas-flow-rate calculation controlling portion 174 outputs a gas-flow rate signal representing a waveform of change of the flow rate FR and a value representing the flow rate FR (e.g., the average value, maximum value or minimum value of the flow rate FR) to the display output device 116. FIG. 31 shows, by way of example, the waveform of the gas-flow rate signal, which was obtained from a rat.

As described above, in the airway gas-flow rate measuring device 110 of the present embodiment, the heater elements (first heater elements) 144a, 144b are provided on the outer circumferential surface of the flexible circuit substrate film (first circuit substrate film) 142, which is wound on the outer circumferential surface of the distal end portion (first sensor substrate) of the gas-flow measuring catheter 124 such that the circuit substrate film 142 has the cylindrical shape and is fixed to the outer circumferential surface of the distal end portion of the gas-flow measuring catheter 124, and the diameter expansion basket 129, whose diameter is increased with the operating wire 128 passing through the fluid measuring catheter 124 being operatively caused to protrude, causes the gas-flow sensor (first gas-flow sensor) 126 to be positioned in a center of the airway 120. Thus, as compared with a conventional type in which the measured gas is caused to pass between a vent hole, which is formed in a side face of a cylindrical sensor substrate that is fixed at one of its opposite ends to a catheter, and an opening of the other of the opposite ends of the cylindrical sensor substrate, it is possible to establish a construction which reduces a flow resistance in the airway 120 and which hardly causes retention of a viscous liquid in the airway 120 and clogging of the airway 120, whereby the measurement of the gas-flow rate can be made accurately and easily.

In the airway gas-flow rate measuring device 110 of the present embodiment, the circuit substrate film (first circuit substrate film) 142 is wound on the outer circumferential surface of the distal end portion (first sensor substrate) of the gas-flow measuring catheter 124 via the spacers 140 such that the circuit substrate film 142 has a cylindrical shape and is fixed to the outer circumferential surface of the distal end portion of the gas-flow measuring catheter 124. A space S is defined between the outer circumferential surface of the distal end portion (first sensor substrate) of the gas-flow measuring catheter 124 and at least portions of the circuit substrate film (first circuit substrate film) 142 in which the heater elements 144a, 144b (first heater elements) are provided. Owing to this arrangement, the distal end portion of the gas-flow measuring catheter 124 is thermally insulated from the heater elements 144a, 144b provided on the circuit substrate film 142 by an increased degree, whereby the gas-flow rate can be more accurately measured. Further, since a heat capacity of the heater elements 144a, 144b themselves is small, a high-speed response can be obtained.

In the airway gas-flow rate measuring device 110 of the present embodiment, the circuit substrate film (first circuit substrate film) 142 is provided with the pair of heater elements 144a, 144b (first heater elements) formed thereon. Further, the airway gas-flow rate measuring device 110 includes the gas-flow-speed measuring circuit (first gas-flow-speed measuring circuit) 150 and the gas-flow-rate calculation controlling portion (first gas-flow-rate calculation controlling portion) 174. The gas-flow-speed measuring circuit 150 includes the first and second bridge circuits 152, 162 as a pair of bridge circuits and the differential amplifier 170. Each of the bridge circuits 152, 162 consists four resistance elements that include a corresponding one of the heater elements 144a, 144b (first heater elements). The differential amplifier 170 is configured to output an output signal corresponding to a difference between output signals of the respective first and second bridge circuits 152, 162. The gas-flow-rate calculation controlling portion 174 is configured to calculate the gas-flow rate signal (first gas-flow-rate signal) representing the flow rate of the gas passing through the airway 120, in accordance with the pre-stored relationship and based on the output signals Vout1, Vout2 of the respective first and second bridge circuits 152, 162. This gas-flow rate signal represents the direction of the gas flow through the airway in one respiratory cycle, by one peak and one trough, irrespective of the direction of the gas flow through the airway. Thus, since the flow rate in one respiratory cycle is represented by one peak and one trough, it is possible to obtain easily understandable flow rate in the airway 120.

Embodiment 61

Figure 32:
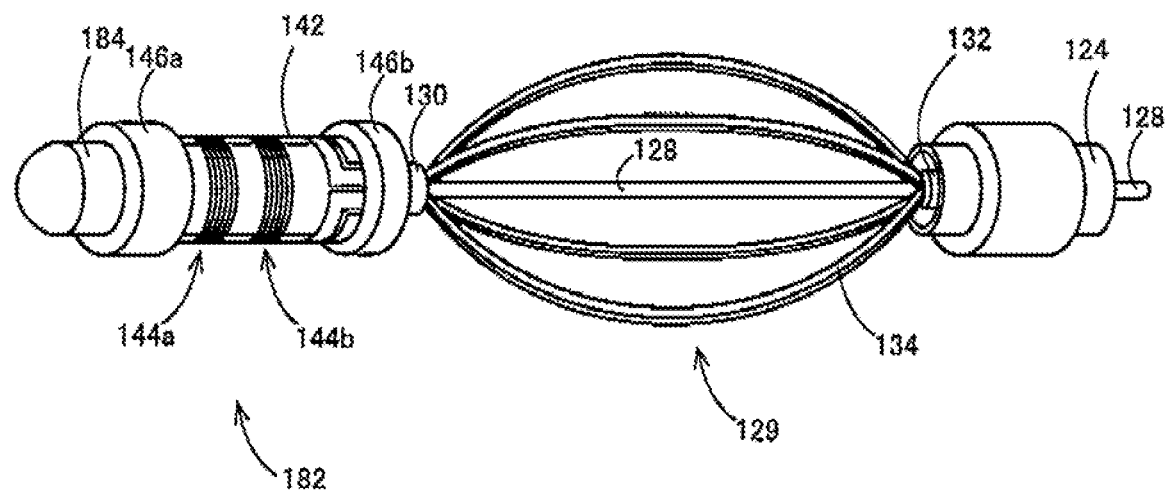
FIG. 32 is a perspective view explaining a construction of a gas-flow sensor according to another embodiment of the invention, and corresponding to the view of FIG. 24.

FIG. 32 is a perspective view explaining a gas-flow sensor 182 according to another embodiment of the invention, which is to be used in the airway gas-flow rate measuring device 110, and corresponding to the view of FIG. 24. The gas-flow sensor 182 of the present embodiment is substantially the same as the above-described gas-flow sensor 126 in construction, but is different from the gas-flow sensor 126 in that the gas-flow sensor 182, in place of the gas-flow sensor 126, is fixed to the distal end tip 130 of the diameter expansion basket 129 and is positioned on a distal-end side of the diameter expansion basket 129 in a state for measurement, and in that the operating wire 128 is connected to the distal end tip 130 of the diameter expansion basket 129 and the rear end tip 132 is slidably disposed on the operating wire 128.

To the distal end tip 130, there is connected a cylindrical substrate 184 that functions as a second sensor substrate. The cylindrical substrate 184 has a same diameter as the gas-flow measuring catheter 124, but is a member independent from the gas-flow measuring catheter 124. The gas-flow sensor 182, which has a construction similar to that of the gas-flow sensor 126, is provided on the cylindrical resin substrate 184. In a state when the operating wire 128 is drawn into the gas-flow measuring catheter 124, the diameter expansion basket 129 is accommodated in the longitudinally-extending through-hole 136 while the cylindrical substrate 184 or the distal end tip 130 (to which the cylindrical substrate 184 is fixed) is substantially in contact with the distal end face of the gas-flow measuring catheter 124. In a state for the measurement in which the operating wire 128 is caused to protrude from the distal end face of the gas-flow measuring catheter 124, the diameter expansion basket 129 is caused to expand with the gas-flow sensor 182 being positioned on the distal end side of the diameter expansion basket 129, as shown in FIG. 32.

As in the above-described embodiments shown in FIGS. 21 and 30, the gas-flow sensor 182 of the present embodiment is connected to the gas-flow-speed measuring circuit 150, and the gas-flow rate is measured by the gas-flow-rate calculation controlling portion 74 of the electronic control device 112, based on the signal supplied from the gas-flow-speed measuring circuit 150. The measured gas-flow rate is displayed in the display output device 116.

In the gas-flow sensor 182 of the present embodiment, the heater elements (second heater elements) 144a, 144b are provided on the outer circumferential surface of the flexible circuit substrate film (second circuit substrate film) 142, which is fixedly wound on the cylindrical substrate (second sensor substrate) 184 to have a cylindrical shape. The diameter expansion basket 129, whose diameter is increased when the operating wire 128 passing through the fluid measuring catheter 124 is operatively caused to protrude from the fluid measuring catheter 124, causes the gas-flow sensor (second gas-flow sensor) 182 to be positioned in a center of the airway 120. Thus, as compared with a conventional type in which the measured gas is caused to pass between a vent hole, which is formed in a side face of a cylindrical sensor substrate that is fixed at one of its opposite ends to a catheter, and an opening of the other of the opposite ends of the cylindrical sensor substrate, it is possible to establish a construction which reduces a flow resistance in the airway 120 and which hardly causes retention of a viscous liquid in the airway 120 and clogging of the airway 120, whereby the measurement of the gas-flow rate can be made accurately and easily. Particularly, the gas-flow sensor 182 is positioned on the distal end side of the diameter expansion basket 129, so that the gas-flow sensor 182 is positioned on an upstream side of the diameter expansion basket 129 in an exhalation period whereby the gas-flow rate in the exhalation period can be more accurately measured.

In the gas-flow sensor 182 according to the present embodiment, the circuit substrate film (second circuit substrate film) 142 is wound on the outer circumferential surface of the cylindrical substrate (second sensor substrate) 184 via the spacers 140 so as to have a cylindrical shape and to be fixed to the outer circumferential surface of the cylindrical substrate 184. Thus, a space S is defined between the outer circumferential surface of the cylindrical substrate (second sensor substrate) 184 and at least portions of the circuit substrate film 142 (second circuit substrate film) in which the pair of heater elements 144a, 144b are provided, so that the cylindrical substrate (second sensor substrate) 184 is thermally insulated from the heater elements 144a, 144b provided on the circuit substrate film 142 by an increased degree, whereby the gas-flow rate can be more accurately measured. Further, since the heat capacity of each of the heater elements 144a, 144b as such is low so that a high-speed response can be obtained.

In the gas-flow sensor 182 of the present embodiment, the pair of heater elements 144a, 144b (second heater elements) are provided on the circuit substrate film (second circuit substrate film) 142. Further, there are provided the gas-flow-speed measuring circuit (second gas-flow-speed measuring circuit) 150 and the gas-flow-rate calculation controlling portion (second gas-flow-rate calculation controlling portion) 174. The gas-flow-speed measuring circuit 150 includes the first and second bridge circuits 152, 162 as a pair of bridge circuits and the differential amplifier 170. Each of the bridge circuits 152, 162 consists four resistance elements that include a corresponding one of the heater elements 144a, 144b (second heater elements). The differential amplifier 170 is configured to output an output signal corresponding to a difference between output signals of the respective first and second bridge circuits 152, 162. The gas-flow-rate calculation controlling portion 174 is configured to calculate the gas-flow rate signal (second gas-flow-rate signal) representing the flow rate of the gas passing through the airway 120, in accordance with the pre-stored relationship and based on the output signals Vout1, Vout2 of the respective first and second bridge circuits 152, 162. This gas-flow rate signal represents the flow rate in one respiratory cycle by one peak and one trough, irrespective of the direction of the gas flow through the airway. Thus, it is possible to obtain easily understandable flow rate in the airway 120.

Embodiment 7

Figure 33:
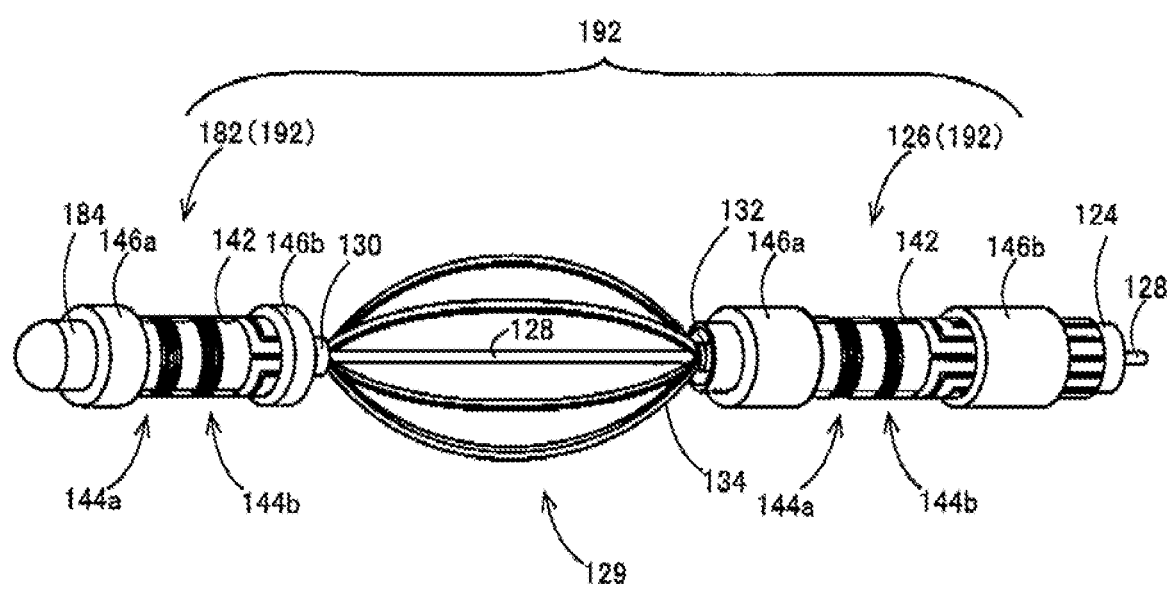
FIG. 33 is a perspective view explaining a construction of a gas-flow sensor according to another embodiment of the invention, and corresponding to the view of FIG. 24.
Figure 34:
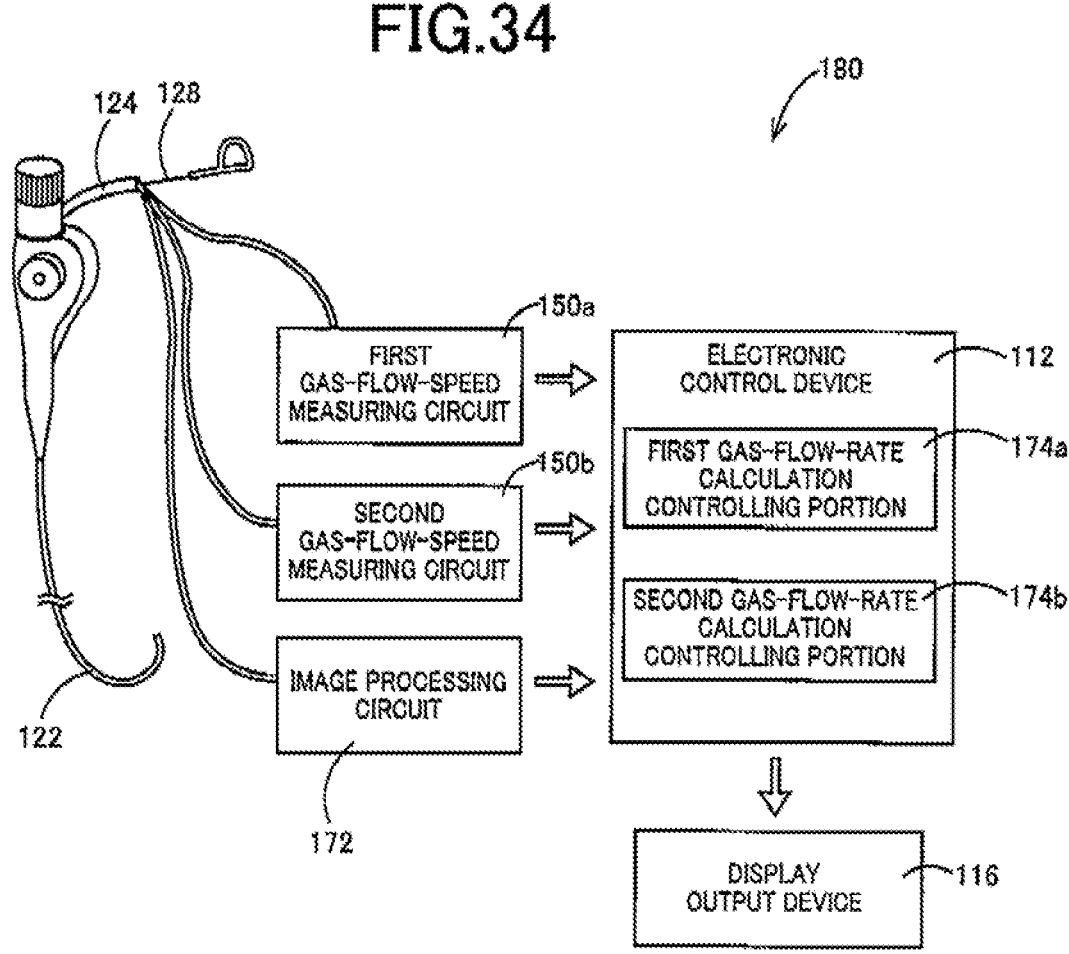
FIG. 34 is a perspective view corresponding to the view of FIG. 24 and explaining a construction of a airway gas-flow rate measuring device in case of use of the gas-flow sensor of the embodiment shown in FIG. 33.

FIG. 33 is a perspective view explaining a gas-flow sensor 192 according to another embodiment of the invention, which is to be used in the airway gas-flow rate measuring device 180, and corresponding to the view of FIG. 24. The gas-flow sensor 192 of the present embodiment is constructed by combining the gas-flow sensor 126 of Embodiment 5 and the gas-flow sensor 182 of Embodiment 6. FIG. 34 is a view explaining a construction of the airway gas-flow rate measuring device 180 of the present embodiment and corresponding to the view of FIG. 21. In FIG. 34, a first gas-flow-speed measuring circuit 150a and a second gas-flow-speed measuring circuit 150b are connected to the gas-flow sensor 126 and the gas-flow sensor 182, respectively. Each of the first and second gas-flow-speed measuring circuits 150a, 150b has substantially the same construction as the gas-flow-speed measuring circuit 150 of the above-described embodiment. Further, each of a first gas-flow-rate calculation controlling portion 174a and a second gas-flow-rate calculation controlling portion 174b has substantially the same functions as the gas-flow-rate calculation controlling portion 174 of the above-described embodiment.

In the airway gas-flow rate measuring device 110 device 180 of the present embodiment, it is possible to obtain substantially the same effects as in the airway gas-flow rate measuring device 110 of Embodiment 5. Further, the gas-flow sensor 182 is positioned on the distal end side of the diameter expansion basket 129, so that the gas-flow sensor 182 is positioned on an upstream side of the diameter expansion basket 129 in an exhalation period whereby the gas-flow rate in the exhalation period can be more accurately measured. Meanwhile, the gas-flow sensor 126 is positioned on the proximal end side of the diameter expansion basket 129, so that the gas-flow sensor 126 is positioned on an upstream side of the diameter expansion basket 129 in an inhalation period whereby the gas-flow rate in the inhalation period can be more accurately measured.

Embodiment 8

Figure 35:
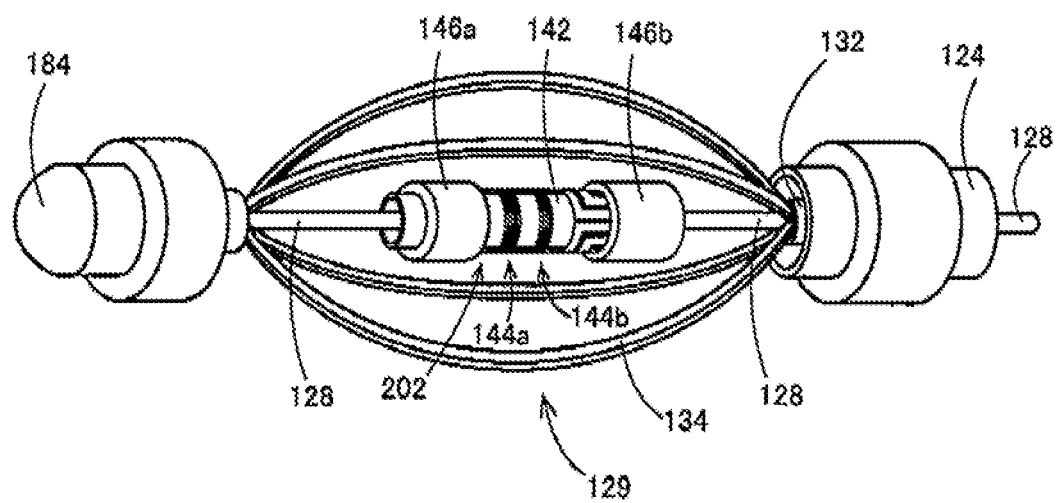
FIG. 35 is a perspective view corresponding to the view of FIG. 24 and explaining a construction of a gas-flow sensor according to another embodiment of the invention.

FIG. 35 is a perspective view explaining a gas-flow sensor 202 according to another embodiment of the invention, which is to be used in the airway gas-flow rate measuring device 110, and corresponding to the view of FIG. 24. The gas-flow sensor 202 of the present embodiment is substantially the same as the above-described gas-flow sensor 126 in construction, but is different from the gas-flow sensor 126 in that the gas-flow sensor 202 is held by the operating wire 128 so as to be positioned in a central portion of the diameter expansion basket 129 in a longitudinal direction of the diameter expansion basket 129 and so as to be positioned in a central portion of a transverse cross-section of the diameter expansion basket 129 in a state for the measurement, and in that the diameter expansion basket 129 and the gas-flow sensor 202 are accommodated in the gas-flow measuring catheter 124 when the operating wire 128 is drawn into the gas-flow measuring catheter 124.

As in the above-described embodiments shown in FIGS. 21 and 30, the gas-flow sensor 202 of the present embodiment is connected to the gas-flow-speed measuring circuit 150, and the gas-flow rate is measured by the gas-flow-rate calculation controlling portion 74 of the electronic control device 112, based on the signal supplied from the gas-flow-speed measuring circuit 150. The measured gas-flow rate is displayed in the display output device 116.

The airway gas-flow rate measuring device 110 of the present embodiment includes: the cylindrical-shaped gas-flow measuring catheter (first sensor substrate) 124 provided integrally or independently in a distal end portion of the gas-flow measuring catheter 124 that passes through the flexible sheath 122; the operating wire 128 provided to protrude from a distal end of the gas-flow measuring catheter 124 and to be introduced from the distal end of the gas-flow measuring catheter 124; the diameter expansion basket 129 which is constituted by the plurality of elastic wires 134 bundled at distal and rear end portions thereof to each other, which is provided in a distal end portion of the operating wire 128, and which has a diameter that is increased when the diameter expansion basket 129 is caused to protrude from a distal end of the gas-flow measuring catheter 124; the flexible circuit substrate film 142 (first circuit substrate film) wound on a portion of the operating wire 128 which is positioned in a central portion of the diameter expansion basket 129 in a longitudinal direction of the diameter expansion basket 129 such that the circuit substrate film 142 has a cylindrical shape and is fixed to the portion of the operating wire 128; and the gas-flow sensor 202 including one first heater element that is provided on an outer circumferential surface of the circuit substrate film 142 or two first heater elements that are provided on the outer circumferential surface of the circuit substrate film 142.

In the present embodiment, the gas-flow sensor 202 is positioned in a center of the airway 120, thereby establishing a construction which reduces a flow resistance in the airway 120 and which hardly causes retention of a viscous liquid in the airway 120 and clogging of the airway 120, whereby the measurement of the gas-flow rate can be made accurately and easily. Particularly, the gas-flow sensor 202 is positioned in a center of the diameter expansion basket 129 in the axial direction and in the transverse cross-section of the diameter expansion basket 129, so that the gas-flow rate can be more accurately measured.

While the embodiments of the present invention have been described above, it is to be understood that the present invention may be embodied otherwise.

For example, in the above-described embodiments, the waveform analysis controlling portion 72 is configured to compose the heartbeat signal SH from the frequency components of heartbeat synchronization waveforms contained in the frequency spectrum obtained from the respiratory waveform. However, the waveform analysis controlling portion 72 may be configured to extract the heartbeat signal SH from the respiration signal SR through a bandpass filter that allows passage therethrough a frequency range including the fundamental frequency of the heartbeat signal SH. The thus extracted heartbeat signal SH has a waveform whose accuracy is not so high. However, for example, in a case where the heart rate HR is to be calculated, the purpose can be sufficiently attained. Further, the cardiac output is estimated based on the amplitude of the heartbeat signal SH.

In the above-described embodiments, the distal end portion itself of the gas-flow measuring catheter 124 functions as the first sensor substrate or second sensor substrate of the gas-flow sensor 126. However, an independent member, which is connected to the distal end portion of the gas-flow measuring catheter 124 in the longitudinal direction or is provided to cover an outer periphery of the distal end portion of the gas-flow measuring catheter 124, may function as the first sensor substrate or second sensor substrate of the gas-flow sensor 126. That is, the sensor substrate of the gas-flow sensor 126 may be provided either integrally or independently in the distal end portion of the gas-flow measuring catheter.

It is possible to employ a system in which the diameter expansion basket and the gas-flow sensor are connected to each other and are disposed in a distal end portion of the operating wire 128 and in which, as shown in the gas-flow sensor 202, the gas-flow sensor is caused to pass through the flexible sheath 122 of the bronchoscope with the entirety of the gas-flow sensor is accommodated in the gas-flow measuring catheter 124, and the diameter expansion basket and the gas-flow sensor are caused, when being positioned in a position for measuring the gas flow, to protrude from a distal end of the gas-flow measuring catheter 124, by the operating wire 128, whereby the diameter of the diameter expansion basket 129 is increased. This arrangement may be applied to the gas-flow sensors 126, 182, 192 except the gas-flow sensor 202.

In the gas-flow-speed measuring circuit 150 of FIG. 30, a temperature compensation circuit is provided as needed for restraining influence of an air temperature on the measured value.

The gas-flow sensor 36 described in Embodiments 1 through 4 and the basket-type gas-flow sensors 126, 182, 192, 202 described in Embodiments 5 through 8 may be provided in balloon catheter, Swan-Ganz catheter and an infusion tube of a drip infusion device, so as to be used to detect a flow speed in an urinary tract, a flow speed in a blood vessel or a flow speed of an infusion.

While the embodiments of the present invention have been described above for illustrative purpose only, it is to be understood that the present invention may be embodied with various changes and improvements, in a range without departing from the spirit of the invention.

DESCRIPTION OF REFERENCE SIGNS

10, 118: living body 24: lungs 26: heart 30: heartbeat-signal detecting device 36, 126, 182, 192, 202: gas-flow sensor 38: gas-flow-speed measuring circuit 40: electronic control device 42: artificial respirator 50: circuit substrate film 52*a*, 52*b*: heater elements 56: bridge circuit 70: flow-rate calculation controlling portion 72: waveform analysis controlling portion 74: heartbeat-signal evaluation controlling portion FR: gas-flow rate SH: heartbeat signal SR: respiration signal SR0: ventilation component signal 110, 180: airway gas-flow rate measuring device 112: electronic control device 114: bronchoscope 116: display output device 120: airway 122: flexible sheath 123: longitudinally-extending through-hole 124: gas-flow measuring catheter (first sensor substrate) 125: light source 127: CCD camera 128: operating wire 129: diameter expansion basket 130: distal end tip 132: rear end tip 134: elastic wire 136: longitudinally-extending through-hole 138: opening 140: spacer 142: circuit substrate film (first circuit substrate film, second circuit substrate film) 144*a*, 144*b*: heater elements (first heater element, second heater element) 146*a*, 146*b*: annular fixing members 150: gas-flow-speed measuring circuit 152: first bridge circuit 154: first voltage regulator 156: first feedback amplifier 158: first measuring circuit 162: second bridge circuit 164: second voltage regulator 166: second feedback amplifier 168: second measuring circuit 170: differential amplifier 172: image processing circuit 174: gas-flow-rate calculation controlling portion 184: cylindrical substrate (second sensor substrate) S: space

The invention claimed is:

1. A heartbeat-signal detecting device for detecting a heartbeat signal of a living body, said heartbeat-signal detecting device comprising:

a gas-flow sensor configured to detect a flow rate of exhalation and inhalation passing through a trachea of the living body in a state in which an artificial respirator is not provided;

a gas-flow calculation controlling portion configured to output a cyclic respiration signal that reflects a respiratory motion of the living body, based on a signal outputted from said gas-flow sensor;

a waveform analysis controlling portion configured to extract, from the cyclic respiration signal outputted from said gas-flow calculation controlling portion, a plurality of frequency components which are in synchronization with a pulse of a heart of the living body superimposed on the cyclic respiration signal, and to output a heartbeat signal representing a heartbeat waveform of the living body, from the plurality of frequency components; and a heartbeat-signal evaluation controlling portion configured to evaluate a functional abnormality or an anatomic abnormality of the heart, based on the heartbeat signal analyzed by said waveform analysis controlling portion, wherein said gas-flow sensor is further configured to detect a flow speed of a gas passing through a tube, based on a change of an electric resistance of a heater element that is heated by electricity supplied thereto, the electric resistance being changed depending on the flow speed, said heater element being constituted by an electric resistance element whose electric resistance is changed depending on a temperature, said heater element being provided on an inner surface of a circuit substrate film which is disposed in said tube and which is spaced apart from said tube a predetermined space.

2. The heartbeat-signal detecting device according to claim 1, wherein
said gas-flow sensor is provided in a mask covering a nose and a mouth of the living body, or an endotracheal intubation tube inserted into the trachea of the living body.

3. The heartbeat-signal detecting device according to claim 1, wherein
the circuit substrate film is disposed along an inner wall surface of said tube and which is spaced apart from said inner wall surface by the predetermined space.

4. The heartbeat-signal detecting device according to claim 3, comprising:
a gas-flow-speed measuring circuit including a bridge circuit that includes four resistance elements, each of one or two of said four resistance elements being constituted by said heater element; and wherein
said gas-flow calculation controlling portion is configured to calculate the flow rate or the flow speed in accordance with a pre-stored relationship between the flow rate or the flow speed and an output signal of said gas-flow-speed measuring circuit that reflects a resistance value of said heater element, and based on the output signal of said gas-flow-speed measuring circuit.

5. The heartbeat-signal detecting device according to claim 1, wherein
said waveform analysis controlling portion is configured to remove, from the cyclic respiration signal outputted from said gas-flow calculation controlling portion, the frequency components which are in synchronization with the pulse of the heart of the living body superimposed on the cyclic respiration signal, and output a ventilation component signal representing a lung capacity component originating from a thorax and a thoracic diaphragm of the living body.

6. The heartbeat-signal detecting device according to claim 1, wherein
said waveform analysis controlling portion is configured to extract, by means of Fourier transform, the plurality of frequency components that are in synchronization with the pulse of the heart superimposed on the cyclic respiration signal outputted from said gas-flow calculation controlling portion, and to compose, by means of inverse Fourier transform, the heartbeat signal from the plurality of frequency components.

7. The heartbeat-signal detecting device according to claim 1, wherein:
the cyclic respiration signal represents a cyclic change of the flow rate that is in synchronization with respiration of the living body, and
the heartbeat waveform represented by the heartbeat signal has a fundamental frequency higher than that of a respiratory waveform represented by the cyclic respiration signal and is superimposed on the respiratory waveform represented by the cyclic respiration signal.

* * * * *